(12) United States Patent
Meyer et al.

(10) Patent No.: US 6,268,171 B1
(45) Date of Patent: *Jul. 31, 2001

(54) RECOMBINANT PILC PROTEINS, METHODS FOR PRODUCING THEM AND THEIR USE

(75) Inventors: Thomas Franz Ferdinand Meyer; Thomas Rudel, both of Tübingen; Roland Richard Ryll, Rottenburg; Ina Bärbel Scheuerpflug, Stuttgart, all of (DE)

(73) Assignee: Max-Planck-Gesellschaft zur Forderung der Wissenschaften e.V., Berlin (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/637,732
(22) PCT Filed: Oct. 25, 1994
(86) PCT No.: PCT/EP94/03494
  § 371 Date: Jun. 28, 1996
  § 102(e) Date: Jun. 28, 1996
(87) PCT Pub. No.: WO95/11919
  PCT Pub. Date: May 4, 1995

(30) Foreign Application Priority Data
  Oct. 26, 1993 (DE) .................................................. 43 36 530

(51) Int. Cl.[7] .................................................. C12P 21/00
(52) U.S. Cl. .................. 435/69.1; 435/69.7; 435/69.8; 435/71.1; 435/91.2; 435/91.4; 435/252.3; 435/320.1; 536/23.1; 536/23.7; 536/24.33; 536/24.32; 536/24.1; 536/24.3; 530/413; 530/350
(58) Field of Search ............................. 435/69.1, 252.3, 435/320.1, 69.7, 69.8, 71.1, 91.2, 91.4; 536/23.1, 23.7, 24.33, 24.32, 24.1, 24.3; 530/413, 350

(56) References Cited

U.S. PATENT DOCUMENTS 5,834,591 * 11/1998 Normark et al. ..................... 530/350

FOREIGN PATENT DOCUMENTS

WO 92/13871 * 8/1992 (WO).

OTHER PUBLICATIONS von Heijne et al. (1990) Protein Engineering, 4/2:109–112.*
von Heijne (1986) Nucleic Acids Research, 14/11:4683–4690.*
Pugsley (1993) Microbiological Reviews, 57/1:50–108.*
Jonsson et al. (1991) EMBO Journal, vol. 10, No. 2, pp. 477–488.*
Rudel et al. (1992) Mol. Microbiol., vol. 6, No. 22, pp. 3439–3450.*
Stryer, in Biochemistry, Second Edition (1981), W.H. Freeman and Company, New York, pp. 629–630.*
Hochuli et al. (1987) J. Chromatography, vol. 411, pp. 177–184.*
Meyer et al. (1984) Proc. Natl. Acad. Sci. USA, vol. 81, pp. 6110–6114.*
Jonsson et al. (1993) Accession No. Q28098, n–geneseq26 Database.*
Jonsson et al. (1993) Accession No. Q28099, n–geneseq26 Database.*
Jonsson et al. (1991) The EMBO Journal, vol. 10, No. 2, pp. 477–488.*
Sequence alignment of SEQ ID NO:3 of 08/637732 with SEQ ID NO:6 of US Patent 5,834,591 issued Nov. 10, 1998.*

* cited by examiner

Primary Examiner—Enrique D. Longton
(74) Attorney, Agent, or Firm—Birch, Stewart, Kolasch & Birch, LLP

(57) ABSTRACT

The invention relates to recombinant gene sequences for synthesizing a protein having the biological activity of the PilC protein. Furthermore, the invention relates to DNA recombinant methods for the production of proteins having the biological activity of the PilC protein as well as the tools of molecular biology needed therein. Besides, the invention relates to proteins having the biological activity of the PilC protein and its antibodies. Further embodiments of the invention are pharmaceutical compositions with a content of the mentioned proteins or antibodies. Preferably, these pharmaceutical compositions serve as vaccines for the immunization against pathogenic bacteria bearing type 4 pili. The invention also relates to kits for the detection of bacteria bearing type 4 pili or antibodies directed against them containing the mentioned proteins or antibodies. Finally, the invention relates to cellular receptors for bacteria bearing type 4 pili and analogues thereof.

32 Claims, 16 Drawing Sheets

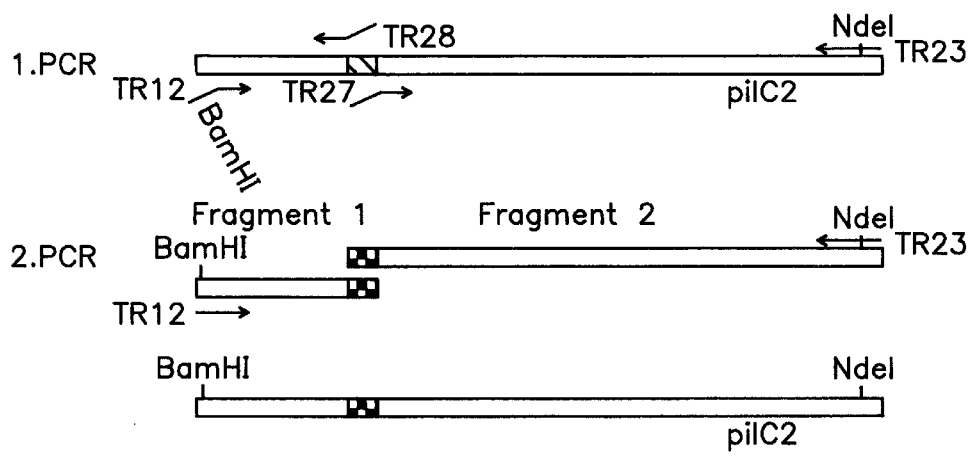

Figure 1A:
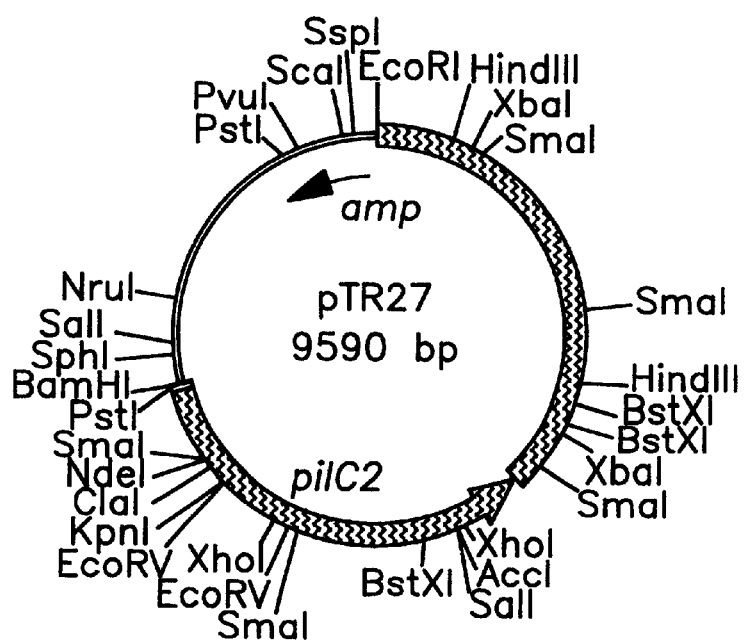

FIG.2A Modification of the homopolymeric, variable nucleotide sequence

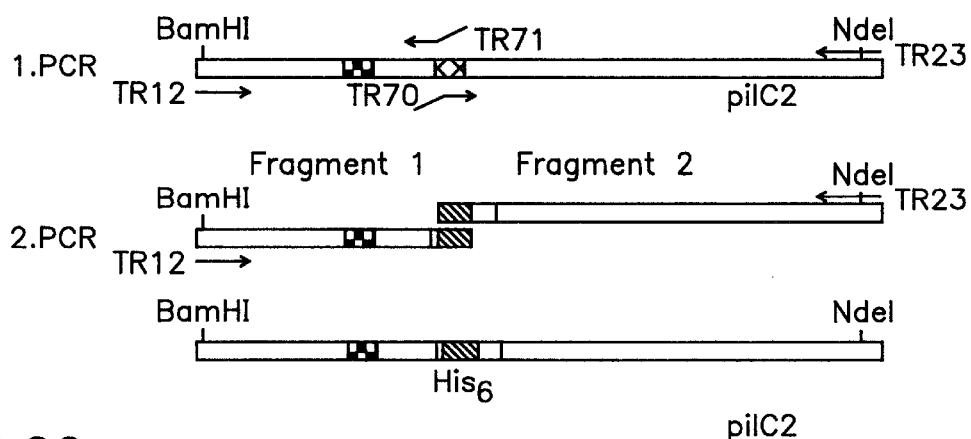

FIG.2B Insertion of a His6-peptide encoding nucleotide sequence

FIG.2C Legend homopolymeric, phase-variable nucleotide sequence ...CAT ACC GGC GGG GGG GGG GGG GCG...
H   T   G   G   G   G   G   A heteropolymeric, non-phase-variable nucleotide sequence ...CAT ACC GGT GGA GGT GGT GGA GCG...
H   T   G   G   G   G   G   A N terminus of the PilC sequence ...GCG CAG GCG CAA ACC CGT AAA TAC...
A   Q   A   Q   T   R   K   Y N terminus of the PilC-His6-peptide encoding nucleotide sequence ...ACC CAT CAC CAC CAT CAT CAC CGT...
T   H   H   H   H   H   H   R processing site of the PilC preform ▲

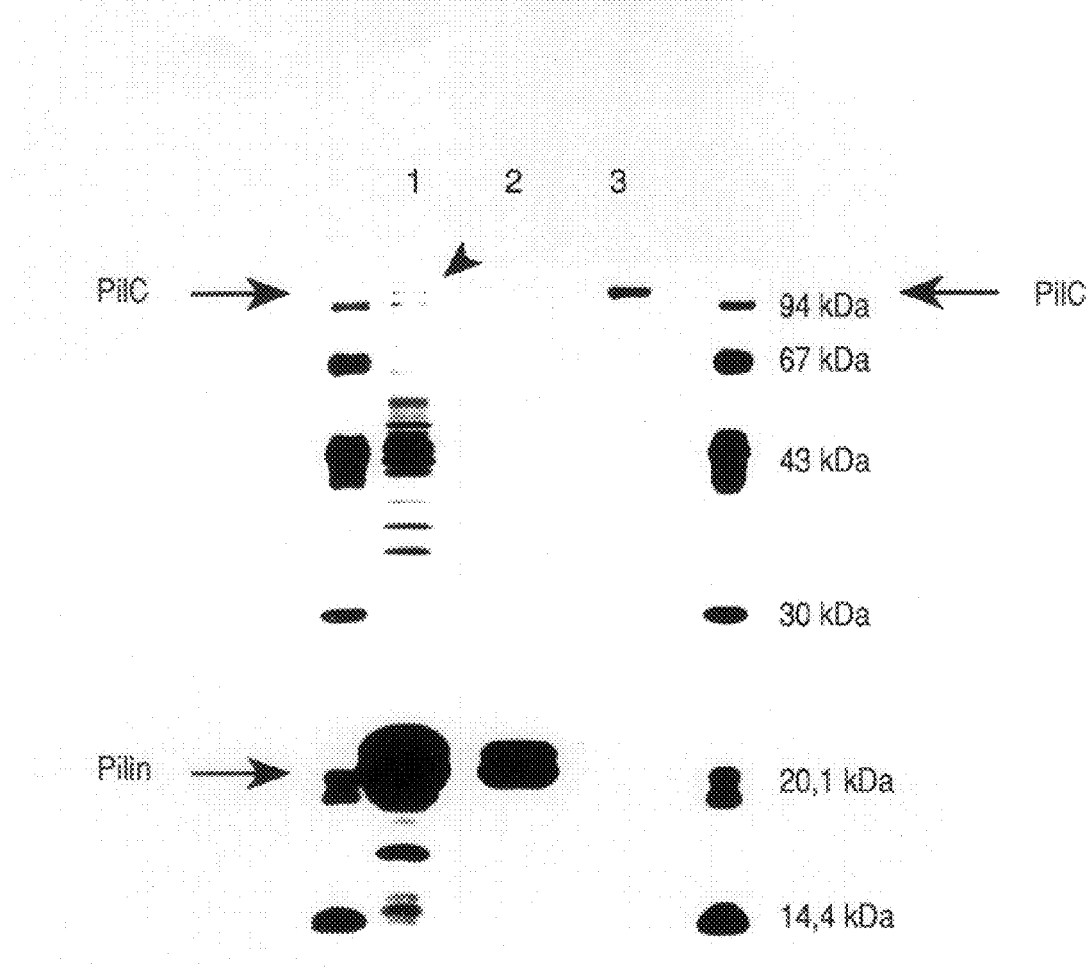

Fig. 4A.1

Figure 4: Nucleotide sequences of pilC1 and pilC2 genes of Neisseria gonorrhoeae (A) and partial nucleotide sequence of a pilC gene of Neisseria meningitidis in comparison with pilC1 (B) and pilC2 (C) of Neisseria gonorrhoeae

A

```
PILC1MS11  - ATGAATAAAACTTTGAAACGGCAGGTTTTCCGCCATACCGCGCTTTATGC   -50
             ||||||||||||| ||| ||| ||||||||||||||||||||||||||||
PILC2MS11  - ATGAATAAAACTTTAAAAAGGCGGGTTTTCCGCCATACCGCGCTTTATGC   -50

PILC1MS11  - CGCCATCTTGATGTTTTCCCATACCGGCGGGGGGGGGGG-CGATGGCGC    -99
             |||||||||||||||||||||||||||||||||||||||  |||||
PILC2MS11  - CGCCATCTTGATGTTTTCCCATACCGGCGGGGGGGGGGGGCGCAGGCGC   -100

PILC1MS11  - AAACCCATCAATACGCTATTATCATGAACGAGCGAAACCAGCCCGAGGTA  -149
             ||||||  | |||||||||||||||||||||||||||| |||||||||||
PILC2MS11  - AAACCCGTAAATACGCTATTATCATGAACGAGCGAAAGCAGCCCGAGGTA  -150

PILC1MS11  - AAGCAGAATGTGCCATCT--TCAAT-------AAAGGACAAAGACAGGAG  -190
             |||  |||  |  |  | ||  |||||      |||||||||| ||||
PILC2MS11  - AAGTGGGAGGGTCAATATAGTCAATCAACATTAAAGGACAAAGGCAGGGA  -200

PILC1MS11  - GCGCGAATATACTTATTATACGCACAGAA-CAGGAGCAGGC---------  -229
             |||   || ||  ||   |  || |||| | ||| | | |
PILC2MS11  - GCGGACATTTAGCCATACGAGCCAGAGAAACTGGAACGGCCAACAAAACA  -250

PILC1MS11  - --TCTGTCTCATTCAACAATAACGATACCCTTGTTTCCCAACAAAGCGGT  -277
             | | ||||||||||||||||| |||| |||||||||| ||||||||||
PILC2MS11  - ATTTTATCTCATTCAACAATAGCGATGAGCTTGTTTCCCGACAAAGCGGT  -300

PILC1MS11  - ACTGCCGTTTTTGGCACAGCCACCTACCTGCCGCCCTACGGCAAGGTTTC  -328
             ||||||||||||||||||||||||||||||||||||||||||||||||||
PILC2MS11  - ACTGCCGTTTTTGGCACAGCCACCTACCTGCCGCCCTACGGCAAGGTTTC  -350

PILC1MS11  - CGGTTTTGATGCCGTCGCTCTGAAAGAGCGCAACAATGCCGTTGATTGGA  -378
             |||||||||||||| || ||||||| ||||| |||||||| ||||||
PILC2MS11  - CGGTTTTGATGCCGACGGGCTGAAAAAGCGCGGCAATGCCGTGAATTGGA  -400

PILC1MS11  - TTCGTACCACCCGCATCGCGCTGGCAGGCTACTCCTACATCGACGTCATA  -428
             ||||||||||||   || |||||||||||| ||||| |||| |||||||
PILC2MS11  - TTCGTACCACCCGGCCCGGGCTGGCAGGCTACATCTACACCGGCGTCATA  -450

PILC1MS11  - TGCAGAAGCTACACAGGC---TGTCCCAAACTTGTCTATAAAACCCGCTT  -475
             ||||||  | ||||||||  || |||  ||||||||||| ||| | ||
PILC2MS11  - TGCAGA-G--ACACAGGGCAATGCCCCGAACTTGTCTATGAGACCAAATT  -497

PILC1MS11  - TACCTTCGGTCAACAAGGGTT-GAAAAGAAAGGCAGGCAGCAAGCTGGAT  -524
             | |||||| |  || ||| |  || || |  || | | ||||||||
PILC2MS11  - TTCCTTCGA-CGGCATCGATTTGGCAAAAGGGGGAAACCGAAAGCTGGAT  -546

PILC1MS11  - ATATACGAAGACAAAAGCCGCGAAAATTCGCCCATTTACAAATTGTCGGA  -574
             |   ||  ||| |||||||||||||||| ||||||||||||||||   |||
PILC2MS11  - AGGCACCCGGACCCAAGCCGCGAAAATTTGCCCATTTACAAATTGAAGGA  -596

PILC1MS11  - TTATCCTTGGTTGGGCGTATCTTTCAATTTGGGCAGCAGAATACCGTCC   -624
             | |||| |||||||||||||||||||||||||||  ||| |||||  |
PILC2MS11  - TCATCCATGGTTGGGCGTATCTTTCAATTTGGGCGGCGAGGGTACCGCCA  -646
```

Fig. 4A.2

```
PILC1MS11 - AAAATAGCAAATTATTCAACAAATTGATATCTTCTTTTAGAGAAGGCAAT -674
            ||  || |||  ||  ||  ||  ||  || |||||||||||||||| |||| ||||
PILC2MS11 - AAGATGGCAGATCATCCAGCAGATGGATATCTTCTTTTAGTGAAGACAAT -696

PILC1MS11 - AATAATCAAACCATCGTCTCTACGACAGAAGGCAACCCTATTTCCCTTGG -724
            |||||||||||||||||||||| |||||||  ||||  ||||||||||||||||
PILC2MS11 - AATAATCAAACCATCGTCTTTACGACACGAGGCCACCCTATTTCCCTTGG -746

PILC1MS11 - CGACCGGCAGCGCGAACATACCGCCGTGGCCTATTATCTGAACGCCAAAC -774
            ||||  ||||||||||||  ||||||||  |||||||||||||  ||||||||
PILC2MS11 - CGACTGGCAGCGCGAAAGTACCGCCATGGCCTATTATCTGGACGCCAAAC -796

PILC1MS11 - TGCACCTGCTGGACAAAAAAGGGATTGAAGATATCGCCCAAGGCAAAATA -824
            ||||||||||||| ||||  | ||||||| ||||||| | ||||||||| |
PILC2MS11 - TGCACCTGCTGGATAAAACACAGATTGAAAATATCGCGCCAGGCAAAACA -846

PILC1MS11 - GTGGATTTGGGTATCTTGAAACCGCACGTCGAGACGAC----AGGACGAA -870
            ||| |||||||  |||||||  ||||| ||||||| | |       ||| |||
PILC2MS11 - GTGAATTTGGGCATCTTGAGACCGCGCGTCGAGGCAAAGGTAAGGCGGAA -896

PILC1MS11 - GCT-----TGCTAGATTTTTGGGCTAGGTGGGACATTAAAGATACCGGGC -915
            |         ||||| |||||||||||| |||||||||||||||||||||||
PILC2MS11 - GTGGGATCTGCTAAATTTTTGGGCTAAGTGGGACATTAAAGATACCGGGC -946

PILC1MS11 - AGATTCCGGTCAAGCTCGGCCTGCCGCAAGTCAAAGCAGGCCGCTGCACC -965
            |||||||||||||||||||||||||| ||||||||||||||||||||||||  |
PILC2MS11 - AGATTCCGGTCAAGCTCGGCCTGCCGGAAGTCAAAGCAGGCCGCTGCATC -996

PILC1MS11 - AACAAACCGAACCCCAATAATAATACCAAAGCCCCTTCGCCGGCACTGAC -1015
            |||||||||||||||||||    ||  |      ||||| |||||||||||||||||
PILC2MS11 - AACAAACCGAACCCCAATCCCAAATC---AGCCCTTTCGCCGGCACTGAC -1043

PILC1MS11 - CGCCCCCGCGCTGTGGTTCGGACCCGGGCAAGATGGTAAGGCGGAGATGT -1065
            ||||||||||||||||||||||| || | |||| |||| |||| | ||||||
PILC2MS11 - CGCCCCCGCGCTGTGGTTCGGCCCTGTGCAAAATGGCAAGGTGCAGATGT -1093

PILC1MS11 - ATTCCGCTTCGGTTTCCACCTACCCCGACAGTTCGAGCAGCCGCATCTTC -1115
            |||||||||||||||||||||||||||||||| ||| |||||||||||||||||||||
PILC2MS11 - ATTCCGCTTCGGTTTCCACCTACCCCGGCAGCTCGAGCAGCCGCATCTTC -1143

PILC1MS11 - CTCCAAGAGCTGAAAACTCAAACCGAACCCGGCAAACCCGGCCGCTATTC -1165
            ||||||||||||||||||| |||||| ||||  |    |||||||| ||||
PILC2MS11 - CTCCAAGAGCTGAAAACTAAAACCGACCCCGCCCGGCCCGGCCGGCATTC -1193

PILC1MS11 - CCTCAAATCTTTGAATGATGGTGAGATTAAAAGTCGACAGCCGAGTTTCA -1215
            ||||     |||||||||      || || |||   ||  ||||||  ||||| ||||
PILC2MS11 - CCTCGCCGCTTTGAATGCGCAGGATATCAAATCCCGCGAGCCGAATTTCA -1243

PILC1MS11 - ACGGCGGCAAACAATCATCCGATTGGATGACGGCGTACATTTGATCAAA -1265
            ||     |||| ||  ||||||||||   | |||||| |    ||||
PILC2MS11 - ACTCAAGGCAGACCGTCATCCGATTGCCGGGCGGCGTGTACCAGATCGCC -1293

PILC1MS11 - CTGAATGGAAGCAAGGATGAGGTCGCCGCTTTTGTCAATTTAAATGGAAA -1315
            | |   ||  |  |  |     ||||||  | ||||        ||||| ||
PILC2MS11 - CCG---GGCAATAGCGGCCGGGTCGCGGGTTTT---------AATGGCAA -1331

PILC1MS11 - CAACACCGGCAAAAACGACACTTTCGGCATTGTTAAGGAAGCGAACGTCA -1365
            ||   |||||||||||||||||||||||||||  |||||   |   |||||
PILC2MS11 - TGAC---GGCAAAAACGACACTTTCGGCATCTACAAGGACAGGCTCGTCA -1378
```

Fig. 4A.3

```
PILC1MS11  - ATCTTGACGCCGACGAGTGGAAAAAAGTGCTGCTGCCTTGGACGGTTCGG  -1415
             | ||| | || ||||||||    |||||||||||||||||||| |||
PILC2MS11  - CACCTGAGGTCGGCGAGTGGAGCGAAGTGCTGCTGCCTTGGACGGCCCGG  -1428

PILC1MS11  - GGTCCCGATAATGACAATAAATTTAAATCAATTAACCAA--AAAC-----  -1458
             |  || |||||||| ||| |||||||| || | |||||||  ||||
PILC2MS11  - TATTACGGTAATGACGATATATTTAAAACATTCAACCAACCAAACAGCAA  -1478

PILC1MS11  - --CAGAAAA-----------ATACAGCCAAAGATACCGCATCCGC----  -1490
             || ||||            |||||||||||| ||||||||||||
PILC2MS11  - AACACAAAACGGCAAAAAACAATACAGCCAAAAATACCGCATCCGCACAA  -1528

PILC1MS11  - --GACAA---CAACGGCAATC---GCGATTTGGGCGACATCGTCAACAGC  -1532
             || ||    ||| | |||    ||||||||||||||||||||||||||
PILC2MS11  - AAGAAAATGACAATGACAAACCCCGCGATTTGGGCGACATCGTCAACAGC  -1578

PILC1MS11  - CCGATTGTCGCGGTCGGCGGGTATTTGGCAACCGCCGCGAACGACGGGAT  -1582
             ||||||||||||||||||||||| |||||||  | || ||||||||||
PILC2MS11  - CCGATTGTCGCGGTCGGCGGGTATCTGGCAACTTCTGCCAACGACGGGAT  -1628

PILC1MS11  - GGTGCATATCTTCAAAAAAAACGGCGGCAGTGATGAACGCAGCTACAATC  -1632
             |||||||||||||||||||| ||||    | ||||||||||||||||||
PILC2MS11  - GGTGCATATCTTCAAAAAAACCGGC---ACGGATGAACGCAGCTACAATC  -1675

PILC1MS11  - TGAAGCTCAGCTACATCCCCGGCACGATGCCGCGCAAGGATATTCAAAGC  -1682
             |||||||||||||||||||||| |||||| ||| ||||||||| || ||
PILC2MS11  - TGAAGCTCAGCTACATCCCCGGTACGATGGAGCGTAAGGATATTGAAGGC  -1725

PILC1MS11  - CAAGAATCCACCCTTGCCAAAGAGCTGCGCGCCTTTGCCGAAAAAGGCTA  -1732
             | || |||   ||| |||||||||||||||| ||||||||||||||||||
PILC2MS11  - AATGACTCCGACCTCGCCAAAGAGCTGCGCACCTTTGCCGAAAAAGGCTA  -1775

PILC1MS11  - TGTGGGCGACCGCTACGGCGTGGACGGCGGCTTTGTCTTGCGCCA-AGTC  -1781
             ||||||||||||||||||||||||||||||||||||||||||||  | |
PILC2MS11  - TGTGGGCGACCGCTACGGCGTGGACGGCGGCTTTGTCTTGCGCCGCATTA  -1825

PILC1MS11  - GAACTGAGCGGG-----CAAAACACGTGTTTATGTTCGGCGCGATGGGT  -1826
             |  ||| | |     ||||||||  | |||||||| || ||||||||
PILC2MS11  - CAGATGACCAAGACAAGCAAAAACATTTCTTTATGTTGGTGCGATGGGC  -1875

PILC1MS11  - TTTGGCGGCAGGGGCGCGTATGCCTTGGATTTAAGCAAAATCAACGGAAA  -1876
             | ||||||| |||||||||||||||||||||||||||||||| || | |
PILC2MS11  - CTGGGCGGCAGAGGCGCGTATGCCTTGGATTTAAGCAAAATCGACAGCAG  -1925

PILC1MS11  - TTATCCGGCCGCCGCCCCCTGTTTGATGTCAAAGATGGCGATAATAACG  -1926
             |  |  ||| ||   || ||||||||||| || |  | | |||||
PILC2MS11  - CAACCTGACCGGCGTTTCCATGTTTGATGTCCAAAACGACAAAATAACA  -1975

PILC1MS11  - GCAAAATC-GCGTGAAA--------GTGGAATTAGGCTACACCGTCGGT  -1967
             ||  ||| |  |||  |       ||| |||||||||||||||||||
PILC2MS11  - ATAACAATAAGAATGACAATAATCGCGTGAAATTAGGCTACACCGTCGGT  -2025

PILC1MS11  - ACGCCGCAAATCGGCAAAATCCGCAACGGCAAATACGCCGCCTTCCTCGC  -2017
             |||||||||||||||||||||| ||||||||||||||||||||||||||
PILC2MS11  - ACGCCGCAAATCGGCAAAACCCAAAACGGCAAATACGCCGCCTTCCTCGC  -2075

PILC1MS11  - CTCCGGTTATGCGGCTAAAAAAATTGACGACTCAACAAATAAAACCGCGC  -2067
             ||||||||||||||||||| ||| |  |         |||| ||||||
PILC2MS11  - TTCCGGTTATGCGGCTAAAAATATTGGCAGCGGCGATAATACAACCGCGC  -2125
```

Fig. 4A.4

```
PILC1MS11 - TGTATGTATATGATTTGAAAGACACCTTAGGTACGCCGATTGCAAAAATC -2117
            |||||||  ||||||||| || |||||    ||||  |  ||||  |||||||
PILC2MS11 - TGTATGTGTATGATTTGGAAAACACCAGTGGTAGTCTGATTAAAAAAATC -2175

PILC1MS11 - GAAGTGAAGGACGGCAAAGGCGGGCTTTCGTCCCCCACGCTGGTGGATAA -2167
            ||||      | |||||||||||||||||||||||||||||||||||||||
PILC2MS11 - GAAGCACCCGGCGGCAAAGGCGGGCTTTCGTCCCCCACGCTGGTGGATAA -2225

PILC1MS11 - AGATTTGGACGGCACGGTCGATATCGCCTATGCCGGCGACCGGGCGGCA -2217
            |||||||||||||||||||||||||||||||||||||||||||||||||||
PILC2MS11 - AGATTTGGACGGCACGGTCGATATCGCCTATGCCGGCGACCGGGCGGCA -2275

PILC1MS11 - ATATGTACCGCTTTGATTTGAGCAATTCCGATTCTAGTAAATGGTCTGCA -2267
            ||||||||||||||||||||||||||||||||||||||||||||||||||
PILC2MS11 - ATATGTACCGCTTTGATTTGAGCAATTCCGATTCTAGTAAATGGTCTGCA -2325

PILC1MS11 - AAGGTTATTTTCGAAGGCGACAAGCCGATTACCTCCGCGCCCGCCGTTTC -2317
            ||||||||||||||||||||||||||||||||||||||||||||||||||
PILC2MS11 - AAGGTTATTTTCGAAGGCGACAAGCCGATTACCTCCGCGCCCGCCGTTTC -2375

PILC1MS11 - CCGACTGGCAGACAAACGCGTCGTCATCTTCGGTACGGGCAGCGATTTGA -2367
            |||||||||||||||||||||| || ||||||||  |||||||||||||||
PILC2MS11 - CCGACTGGCAGACAAACGCGTGGTTATCTTCGGCACGGGCAGCGATTTGA -2425

PILC1MS11 - CCGAAGATGATGTACTGAATACGGGCGAACAATATATTTACGGTATCTTT -2417
            |||  |  ||||||||||  ||||||  ||||||||||||||||||||||
PILC2MS11 - GTGAACAGGATGTACTGGATACGGACAAACAATATATTTACGGTATCTTT -2475

PILC1MS11 - GACGACGATAAGGGGACGGTTAAGGTAACGGTACAAAACGGCACGGCAGG -2467
            |||||||||||    ||||||||| |||| ||||     |||||||||  |||
PILC2MS11 - GACGACGATAAGTCGACGGTTAATGTAAAGGTAACAAACGGCACGGGAGG -2525

PILC1MS11 - CGGGCTGCTCGAGCAACACCTTACTCAGGAAAATAAAACATTATTCCTGA -2517
            |||||||||||||||||    ||||   ||||||  |||||| |||||||||
PILC2MS11 - CGGGCTGCTCGAGCAAGTGCTTAAAGAGGAAAGTAAAACCTTATTCCTGA -2575

PILC1MS11 - ACAAGAG------ATCCGACGGTTCGGGCAGCAAGGGCTGGGCGGTGAAA -2561
            ||| |       |||||  ||| |||| |    ||  || |||| ||||||
PILC2MS11 - GCAATAATAAGGCATCCGGCGGATCGGCCGATAAAGGGTGGGTAGTGAAA -2625

PILC1MS11 - TTGAGGGAAGGAGAACGCGTTACCGTCAAACCGACCGTGGTATTGCGTAC -2611
            ||||||||||||||||||||||||||||||||||||||||||||||||||
PILC2MS11 - TTGAGGGAAGGAGAACGCGTTACCGTCAAACCGACCGTGGTATTGCGTAC -2675

PILC1MS11 - CGCCTTCGTAACCATCCGCAAATATAACGA---CGG-CGGCTGCGGCGCGG -2658
            |||||| || ||||||||||||||||| ||   ||| ||   || |||||||
PILC2MS11 - CGCCTTTGTCACCATCCGCAAATACGGATACGGACAAATGTGGCGCGC -2725

PILC1MS11 - AAACCGCCATTTTGGGCATCAATACCGCCGACGGCGGCGCATTGACTCCG -2708
            ||||||||||||||||||||||||||||||||||||||||||||||||||
PILC2MS11 - AAACCGCCATTTTGGGCATCAATACCGCCGACGGCGGCGCATTGACTCCG -2775

PILC1MS11 - AGAAGCGCGCGCCCGATTGTGCCGGATCACAATTCGGTTGCGCAATATTC -2758
            ||||||||||||||||||||||||||||||||||||||||||||||||||
PILC2MS11 - AGAAGCGCGCGCCCGATTGTGCCGGATCACAATTCGGTTGCGCAATATTC -2825

PILC1MS11 - CGGCCATAAGACAACCTCCAAAGGCAAATCCATCCCTATAGGTTGTATGG -2808
            |||||||| |||  ||  ||||| ||||||||| ||||| || |||
PILC2MS11 - CGGCCATCAGAAAATG---AACGGCAAGTCCATCCCCATAGGCTGCATGT -2872
```

Fig. 4A.5

```
PILC1MS11  - ACAAAGACGGTAAAACCGTCTGCCCGAACGGATATGTTTACGACAAGCCG -2858
             ||| || | |||||||||||||||||||||||||||||||||||| |||
PILC2MS11  - GGAAAAACAGCAAAACCGTCTGCCCGAACGGATATGTTTACGACAAACCG -2922

PILC1MS11  - GTTAATGTGCGTTATCTGGATGAAACGGAAACAGACGGATTTTCAACGAC -2908
             |||||||||||||| ||||| |||| | |||||||||  ||  |    ||
PILC2MS11  - GTTAATGTGCGTTACCTGGACGAAAAGAAAACAGACGATTTCCCCGTCAC -2972

PILC1MS11  - GGCGGACGGCGATGCGGGCGGCAGCGGTATAGACCCCGCCGGCAGGCGTC -2958
             ||| |||||| ||||| |||||||||||||| | |  |   | ||| .  |
PILC2MS11  - GGCAGACGGTGATGCAGGCGGCAGCGGAACATTCAAAGAGGGTAAAAAAC -3022

PILC1MS11  - CCGGCAAAAACAACCGCTGCTTCTCCAAAAAAGGGGTGCGCACCCTGCTG -3008
             ||| | || |||||| ||||||||| |||||| |||||||||||||||||
PILC2MS11  - CCGCCCGCAATAACCGGTGCTTCTCCGGAAAGGTGTGCGCACCCTGCTG -3072

PILC1MS11  - ATGAACGATTTGGACAGCTTGGATATTACCGGCCCGATGTGCGGTATCAA -3058
             |||||||||||||||||||||||||||||||||||||||||||||||||||
PILC2MS11  - ATGAACGATTTGGACAGCTTGGATATTACCGGCCCGATGTGCGGTATCAA -3122

PILC1MS11  - ACGCTTAAGCTGGCGCGAAGTCTTCTTCTGA -3089
             |||||||||||||||||||||||||||||||
PILC2MS11  - ACGCTTAAGCTGGCGCGAAGTCTTCTTCTGA -3153
```

Fig. 4B.1

```
PILC1MS11 - ATGAATAAAACTTTGAAACGGCAGGTTTTCCGCCATACCGCGCTTTATGC  -50
            |||||||||||||| ||| |||||||||||||||||||||||||||||||
PILCA1493 - ATGAATAAAACTTTAAAAAGGCAGGTTTTCCGCCATACCGCGCTTTATGC  -50

PILC1MS11 - CGCCATCTTGATGTTTTCCCATACCGGCGGGGGGGGGGGGCGATGGCGC   -99
            ||||||||||||||||||||||||||||||||||||||    ||||||||||
PILCA1493 - CGCCATCTTGATGTTTTCCCATACCGGCGGGGGGGG---GCGATGGCGC   -96

PILC1MS11 - AAACCCATCAATACGCTATTATCATGAACGAGCGAAACCAGCCCGAGGTA  -149
            ||||||||  ||||||||||||||||||||||||||||||| |||||||
PILCA1493 - AAACCCATAAATACGCTATTATCATGAACGAGCGAAACCAGCTCGAGGTA  -146

PILC1MS11 - AAGCAGAATGTGCCATCTTCAA---TAAAGGACAAAGACAGGAGGCGCGA  -196
            |||  ||||| || || |||||       |||||||||||||||   ||| |
PILCA1493 - AAGGGGAATGGGCAATATTCAACAATAAAGGACAAAGACAGGGAACGCAA  -196

PILC1MS11 - ATATACTTATTATACGCACAGAACAGGAGCAGGCTCTGTCTCATTCAACA  -246
            || || ||| |||   |||||    || | ||||||||||| |   ||| |||
PILCA1493 - ATTTATCTATAATAAAGACAGAGGGGGTGGAGGCTCTGTNTTTTTCGACA  -246

PILC1MS11 - ATAACGATACCCTTGTTTCCCAACAAAGCGGTACTGCCGTTTTTGGCACA  -296
            ||| ||||||||||||||||||||||||| ||||||||||||||||||||||
PILCA1493 - ATACCGATACCCTTGTTTCCCAACAAAGAGGTACTGCCGTTTTTGGCACA  -296

PILC1MS11 - GCCACCTACCTGCCGCCCTACGGCAAGGTTTCCGGTTTTGATGCCGTCGC  -346
            |||||||||||||||||||||||||||||||||||||||||  |||||| ||
PILCA1493 - GCCACCTACCTGCCGCCCTACGGCAAGGTTTCCGGTTTTRATGCCGACGG  -346

PILC1MS11 - TCTGAAAGAGCGCAACAATGCCGTTGATTGGATTCGTACCACCCGCATCG  -396
            ||| || |||||||||||||||||| |||||||||| ||||||||   ||
PILCA1493 - GCTGCAAAAGCGCAACAATGCCGTCGATTGGATTCATACCACCCAGGCCG  -396

PILC1MS11 - CGCTGGCAGGCTACTCCTACATCGACGTCATATGCAGAAGCTACACAGGC  -446
            |||||||||||||| |||||| ||||||||||||||||||||||  | | ||
PILCA1493 - GGCTGGCAGGCTACGCCTACACCGACGTCATATGCAGAAGCAACCAATGC  -446

PILC1MS11 - TGTCCCAAACTTGTCTATAAAACCCGCTTTACCTTCGGTCAACAAGGGTT  -496
               ||| |||||||||||||| | |||   ||| ||||||           || ||
PILCA1493 - ---CCCCAACTTGTCTATGAGACCAAATTTTCCTTCGACGGCATCGGTTT  -493

PILC1MS11 - GAAAAGAAAGGCAGGCAGCAAGCTGGATATATACGAAGACAAAAGCCGCG  -546
            |  || ||| || |||||   |||||||    || |||   ||||||||
PILCA1493 - GGCAAAAAATGCGGGCAGC---CTGGATAGGCACCCGGACCCAAGCCGCG  -540

PILC1MS11 - AAAATTCGCCCATTTACAAATTGTCGGATTATCCTTGGTTGGGCGTATCT  -596
            |||||||||  |||||||||||    ||| |||||  |||||||||||||
PILCA1493 - AAAATTCGCSCATTTACAAATTGAAAGATCATCCATGGTTGGGCGTATCT  -590

PILC1MS11 - TTCAATTTGGGCAGCGAGAATACCGTCCAAAATAGCAAATTATTCAACAA  -646
            |||||||||||||||||||||||||||||  ||  |||||| ||||||||||
PILCA1493 - TTCAATTTGGGCAGCGAGAATACCGTCAAAGATGGCAAATCATTCAACAA  -640

PILC1MS11 - ATTGATATCTTCTTTTAGAGAAGGCAATAATAATCAAACCATCGTCTCTA  -696
            |||||||||||||||||||||  |||||||||||||||||||||||||||||
PILCA1493 - ATTGATATCTTCTTTTAGTGAAGGCAATAATAATCAAACCATCGTCTCTA  -690
```

Fig. 4B.2

```
PILC1MS11  - CGACAGAAGGCAACCCTATTTCCCTTGGCGACCGGCAGCGCGAACATACC  -746
             |||||   ||||  || ||||||||||||  |||||  || ||||||||||||||
PILCA1493  - CGACACGAGGCCACTCTATTTCCCTTAGCGACTGGAAGCGCGAACATACC  -740

PILC1MS11  - GCCGTGGCCTATTATCTGAACGCCAAACTGCACCTGCTGGACAAAAAAGG  -796
             |||  |||||||||||||||||||||||||||||||||||||||||||||||||
PILCA1493  - GCCATGGCCTATTATCTGAACGCCAAACTGCACCTGCTGGACAAAAAAGG  -790

PILC1MS11  - GATTGAAGATATCGCCCAAGGCAAAATAGTGGATTTGGGTATCTTGAAAC  -846
             ||||||||||||||||||||||||||||||  ||||||||||| |  ||||| ||
PILCA1493  - GATTGAAGATATCGCCCAAGGCAAAACAGTGGATTTGGGCACCTTGAGAC  -840

PILC1MS11  - CGCACGTCGAGACGACAGGACGAAGCT------TGCTAGATTTTTGGGCT  -890
             ||| ||||||||  | ||  |  |   |      ||||| |||||||||||
PILCA1493  - CGCGCGTCGAGGCAACGGTAAGGCGGGGGGAGCTGCTAAATTTTTGGGCT  -890

PILC1MS11  - AGGTGGGACATTAAAGATACCGGGCAGATTCCGGTCAAGCTCGGCC-TGC  -949
             | |||| | ||| ||||||  |||  | |||  |     ||  ||||  |||
PILCA1493  - ACGTGGAAGATTGAAGATAAAGGGAACATTACAGTNCGCCTNGGCCCTGC  -940

PILC1MS11  - CGCAAGTCAAAGCAGGCCGCTGCAC-CAACAAACCGAACCCCAATAATAA  -988
             || |||||||||||   || |   ||  |||||||  |||||||||||||    ||
PILCA1493  - CGGAAGTCAAAGCAAGNCGGTTCGTACAACAAAGCGAACCCCAATCCCAA  -990

PILC1MS11  - TACCAAAGCCCCTTCGCCGGCACTGACCGCCCCCGCGCTGTGGTTCGGAC  -1038
             ||||||||||  ||  || ||||||||||||||||||||||||||||||||||
PILCA1493  - CGCCAAAGCCCCCTCCCCCGCACTGACCGCCCCCGCGCTGTGGTTCGGAC  -1040

PILC1MS11  - CCGGGCAAGATGGTAAGGCGGAGATGTATTCCGCTTCGGTTTCCACCTAC  -1088
             |  |   |||||||||||||||||||||||||||||||||||||  ||||||
PILCA1493  - CTGTGAAAGATGGTAAGGCGGAGATGTATTCCGCTTCGGTTTCTACCTAC  -1090

PILC1MS11  - CCCGACAGTTCGAGCAGCCGCATCTTCCTCCAAGAGCTGAAAACTCAAAC  -1138
             ||||||||||||||||||||||||||   ||| ||| | ||||||||    ||||
PILCA1493  - CCCGACAGTTCGAGCAGCCGCATCTACCTTCAAAATCTGAAAAGAAAAAC  -1140

PILC1MS11  - CGAACCCGGCAAACCCGGCCGCTATTCCCTCAAATCTTTGAATGATGGTG  -1188
             |||  ||||||||||||||||||||  ||||||||| || |  ||||  |||    ||
PILCA1493  - CGACCCCGGCAAACCCGGCCGCCATTCCCTCGAAACCTTGACTGAGAATG  -1190

PILC1MS11  - AGATTAAAAGTCGACAGCCGAGTTTCAACGGGCGGCAAACAATCATCCGA  -1238
             |  |||||||||||  ||||||  |||||    ||||||||||||  ||||||||||
PILCA1493  - ATATTAAAAGTCGAGAGCCGAATTTCACAGGGCGGCAAACCATCATCCGA  -1240

PILC1MS11  - TTGGATGACGGCGTACATTTGATCAAACTGAATGGAAGCAAGGATGAGGT  -1288
             |||  |||   ||||||||||  |  |||||||||||||  |||  |||   ||||||
PILCA1493  - TTGAATGGCGGCGTACGTGAGATCAAACTGGATAGAAACAATACTGAGGT  -1290

PILC1MS11  - CGCCGCTTTTGTCAATTTAAATGGAAACAACACCGGCAAAAACGACACTT  -1338
             ||                ||||||||| ||||||||||  ||     ||||| ||||||||
PILCA1493  - CG---------TCAATTTTAATGGAAATGAC---GGCAACAACGACACTT  -1328

PILC1MS11  - TCGGCATTGTTAAGGAAGCGAACGTCAATCTTGACGCCGACGAGTGGAAA  -1388
             ||||||||||||||||    |   ||||  | |||      ||  ||||||||||||||
PILCA1493  - TCGGCATTGTTAAGGACTTGGGCGTCGAACCTGATACCAGCGAGTGGAAA  -1378

PILC1MS11  - AAAGTGCTGCTGCCTTGGACGGTTCGGGGTCCCGATAATGACAATAAATT  -1438
             ||||| |||||||||||||||||||||||||  |  | || ||||||||||||||||
PILCA1493  - AAAGTATTGCTGCCTTGGACGGTTCGGGGTTTTGCTGATGACAATAAATT  -1428
```

Fig. 4B.3

```
PILC1MS11 - TAAATCAATTAACCAAAAACCAGA--------------AAAATACAGCC -1478
            ||||  || |  ||| || ||  | |              ||||||||||
PILCA1493 - TAAAGCATTCAACAAAGAAGAAAACAACGACAACAAGCCAAAATACAGCC -1478

PILC1MS11 - AAAGATACCGCATCCGCGACAACAAC---GGCAATCGCGATTTGGGCGAC -1520
            ||| ||||||||| |||||||||||||   ||| | ||| |||||||||||
PILCA1493 - AAAAATACCGCAGCCGCGACAACAACAAGGGCGAACGCAATTTGGGCGAC -1528

PILC1MS11 - ATCGTCAACAGCCCGATTGTCGCGGTCGGCGGGTATTTGGCAACCGCCGC -1570
            |||||||||||||| || || ||||||||| |||||||||| || ||||
PILCA1493 - ATCGTCAACAGCCCCATCGTGGCGGTCGGCGAGTATTTGGCTACTTCCGC -1578

PILC1MS11 - GAACGACGGGATGGTGCATATCTTCAAAAAAAACGGCGGCAGTGATGAAC -1620
            |||||||||||||||||||||||||||  |||||| |||||||  || | |
PILCA1493 - CAACGACGGGATGGTGCATATCTTCAAACAAAGCGGCGGG---GACAAGC -1625

PILC1MS11 - GCAGCTACAATCTGAAGCTCAGCTACATCCCCGGCACGATGCCGCGCAAG -1670
            ||||||||||||||||||||||||||||||| ||  || ||||||||||||
PILCA1493 - GCAGCTACAATCTGAAGCTCAGCTACATCCCTGGAACGATGCCGCGCAAG -1675

PILC1MS11 - GATATTCAAAGCCAAGAATCCACCCTTGCCAAAGAGCTGCGCGCCTTTGC -1720
            |||||||||| |    |||||||||||||||||||| |||||| |||||||
PILCA1493 - GATATTCAAAACACCGAATCCACCCTTGCCAAAGA-MTGCGCACCTTTGC -1724

PILC1MS11 - CGAAAAAGGCTATGTGGGCGACCGCTACGGCGTGGACGGCGGCTTTGTCT -1770
            ||||||||||||||||||||||||||||||||||||||||||||||||||
PILCA1493 - CGAAAAAGGCTATGTGGGCGACCGCTACGGCGTGGACGGCGGCTTTGTCT -1774

PILC1MS11 - TGCGCCAAGTCGAAC---TGAGCGGGCAAAAACACGTGTTTATGTTCGGC -1817
            |||||  ||||  ||     | |  |||| |||| |  ||||||||||||||
PILCA1493 - TGCGCAAAGTTGATAACTTAAACGGGSAAAACCGCGTGTTTATGTTCGGC -1824

PILC1MS11 - GCGATGGGTTTTGGCGGCAGGGGCGCGTATGCCTTGGATTTAAGCAAAAT -1867
            ||||||||  |||||||||  ||  ||||||||||||||||||||| | ||||
PILCA1493 - GCGATGGGCTTTGGCGGSAGAGGCGCGTATGCCTTGGATTTGACCAAAGC -1874

PILC1MS11 - CAACGGAAATTATCCGGCCGCCGCCCCCTGTTTGATGTCAAAGATGGCG -1917
            |  ||||  |  | |||  ||||||    |||||||||||||| ||||||  ||
PILCA1493 - CGACGGCAGTGACCCGACCGCCGTTTCCCTGTTTGATGTAAAAGATAACG -1924

PILC1MS11 - ATAATAACGGCAAAAATCGCGTGAAAGTGGAATTAGGCTACACCGTCGGT -1967
            ||||| |||||  |||||||||||      ||||||||||||||||||||||
PILCA1493 - GCAATAATGGCAATAATCGCGTG------GAATTAGGCTACACCGTCGGC -1968

PILC1MS11 - ACGCCGCAAATCGGCAAAATCCGCAACGGCAAATACGCCGCCTTCCTCGC -2017
            |||||||||||||| |||| || | ||||||||||||||||||||||||||
PILCA1493 - ACGCCGCAAATCGGSAAAACCCACGACGGCAAATACGCCGCCTTCCTCGC -2018

PILC1MS11 - CTCCGGTTATGCGGCTAAAAAAATTGA---CGACTCAACAAATAAAACCG -2064
            |||||||||||| |||||| ||||| |    | |         ||||||||||
PILCA1493 - CTCCGGTTATGCGACTAAAGAAATTATTACCAGCGGCGACAATAAAACCG -2068

PILC1MS11 - CGCTGTATGTATATGATTTGAAAGACACCTTAGG---TACGCCGATTGCA -2111
            ||||||||| |||||||||| | ||||   ||  | |    || | |||| |
PILCA1493 - CGCTGTATGTGTATGATTTGGAAGGAAACGGTACGAATAATCTGATTAAA -2118

PILC1MS11 - AAAATCGAAGTGAAGGACGGCAAAGGCGGGCTTTCGTCCCCCACGCTGGT -2161
            |||||||||||    | |||||| |||||||||||||||||||||||||||
PILCA1493 - AAAATCGAAGTACCCGGCGGCAAGGGCGGGCTTTCGTCCCCCACGCTGGT -2168
```

Fig. 4B.4

```
PILC1MS11 - GGATAAAGATTTGGACGGCACGGTCGATATCGCCTATGCCGGCGACCGGG -2211
            ||||||||||||||||||||||||||||||||||||||||||||| || |
PILCA1493 - GGATAAAGATTTGGACGGCACGGTCGATATCGCCTATGCCGGCGATCGCG -2218

PILC1MS11 - GCGGCAATATGTACCGCTTTGATTTGAGCAATTCCGATTCTAGTAAATGG -2261
            ||||  |||||||||||||||||||||||||||| |   ||| ||    |||||
PILCA1493 - GCGGGAATATGTACCGCTTTGATTTGAGCAGTCAAGATCCTCAACAATGG -2268

PILC1MS11 - TCTGCAAAGGTTATTTTCGAAGGCG-ACAAGCCGATTACCTCCGCGCCCG -2310
            |||| |     ||||||| ||||||  | ||  |||||||| ||||||||||
PILCA1493 - TCTGTACGCACTATTTTTGAAGGCACAAAACCCGATTACTTCCGCGCCCG -2318

PILC1MS11 - CCGTTTCCCGACTGGCAGACAAACGCGTCGTCATCTTCGGTACGGGCAGC -2360
            |   |||
PILCA1493 - CTATTT                                              -2324
```

Fig. 4C.1

C

```
PILC2MS11 - ATGAATAAAACTTTAAAAAGGCGGGTTTTCCGCCATACCGCGCTTTATGC -50
            ||||||||||||||||||||||||| ||||||||||||||||||||||||
PILCA1493 - ATGAATAAAACTTTAAAAAGGCAGGTTTTCCGCCATACCGCGCTTTATGC -50

PILC2MS11 - CGCCATCTTGATGTTTTCCCATACCGGCGGGGGGGGGGGCGCAGGCGC   -100
            ||||||||||||||||||||||||||||||||||||||||    ||  |||||
PILCA1493 - CGCCATCTTGATGTTTTCCCATACCGGCGGGGGGGG----CGATGGCGC  -96

PILC2MS11 - AAACCCGTAAATACGCTATTATCATGAACGAGCGAAAGCAGCCCGAGGTA -150
            ||||||  ||||||||||||||||||||||||||||||| ||||  |||||||
PILCA1493 - AAACCCATAAATACGCTATTATCATGAACGAGCGAAACCAGCTCGAGGTA -146

PILC2MS11 - AAGTGGGAGGGTCAATATAGTCAATCAACATTAAAGGACAAAGGCAGGGA -200
            |||  ||  |  ||  |||||||       |||||| |||||||||||| ||||||
PILCA1493 - AAGGGGAATGGGCAATAT------TCAACAATAAAGGACAAAGACAGGGA -190

PILC2MS11 - GCGGACATTTAGCCATACGAGCCAGAGAAACTGGAACGGCCAACAAAACA -250
            ||  |  ||||||  |  |||  |      |  |||      |      |||
PILCA1493 - ACGCAAATTTATCTATAATAAAGACAGAGGGGGTGGAGGC---------- -230

PILC2MS11 - ATTTTATCTCATTCAACAATAGCGATGAGCTTGTTTCCCGACAAAGCGGT -300
              |  |  |   |||  ||||||| ||||    |||||||||| |||||| |||
PILCA1493 - --TCTGTNTTTTTCGACAATACCGATACCCTTGTTTCCCAACAAAGAGGT -278

PILC2MS11 - ACTGCCGTTTTTGGCACAGCCACCTACCTGCCGCCCTACGGCAAGGTTTC -350
            ||||||||||||||||||||||||||||||||||||||||||||||||||
PILCA1493 - ACTGCCGTTTTTGGCACAGCCACCTACCTGCCGCCCTACGGCAAGGTTTC -328

PILC2MS11 - CGGTTTTGATGCCGACGGGCTGAAAAAGCGCGGCAATGCCGTGAATTGGA -400
            |||||||  ||||||||||||||| |||||||  |||||||||  |||||||
PILCA1493 - CGGTTTTRATGCCGACGGGCTGCAAAAGCGCAACAATGCCGTCGATTGGA -378

PILC2MS11 - TTCGTACCACCCGGCCCGGGCTGGCAGGCTACATCTACACCGGCGTCATA -450
            |||  ||||||||  | |||||||||||||||||    ||||||||| |||||||
PILCA1493 - TTCATACCACCCAGGCCGGGCTGGCAGGCTACGCCTACACCGACGTCATA -428

PILC2MS11 - TGCAGAGACACAGGGCAATGCCCCGAACTTGTCTATGAGACCAAATTTTC -500
            ||||||  ||         ||||||||| |||||||||||||||||||||||
PILCA1493 - TGCAGAAGCAA---CCAATGCCCCCAACTTGTCTATGAGACCAAATTTTC -475

PILC2MS11 - CTTCGACGGCATCGATTTGGCAAAAGGGGGAAACCGAAAGCTGGATAGGC -550
            ||||||||||||||| |||||||||       |   |  |   ||||||||||
PILCA1493 - CTTCGACGGCATCGGTTTGGCAAAAAATGCGGGCAGC---CTGGATAGGC -522

PILC2MS11 - ACCCGGACCCAAGCCGCGAAAATTTGCCCATTTACAAATTGAAGGATCAT -600
            |||||||||||||||||||||||| || |||||||||||||||| ||||||
PILCA1493 - ACCCGGACCCAAGCCGCGAAAATTCGCSCATTTACAAATTGAAAGATCAT -572

PILC2MS11 - CCATGGTTGGGCGTATCTTTCAATTTGGGCGGCGAGGGTACCGCCAAAGA -650
            |||||||||||||||||||||||||||||| || |||||  ||||| ||||||
PILCA1493 - CCATGGTTGGGCGTATCTTTCAATTTGGGCAGCGAGAATACCGTCAAAGA -622

PILC2MS11 - TGGCAGATCATCCAGCAGATGGATATCTTCTTTTAGTGAAGACAATAATA -700
            |||||  ||||| ||  ||  ||  ||||||||||||||||||| ||||||||
PILCA1493 - TGGCAAATCATTCAACAAATTGATATCTTCTTTTAGTGAAGGCAATAATA -672
```

Fig. 4C.2

```
PILC2MS11 - ATCAAACCATCGTCTTTACGACACGAGGCCACCCTATTTCCCTTGGCGAC -750
            ||||||||||||||||| |||||||||||||||| ||||||||||| |||||
PILCA1493 - ATCAAACCATCGTCTCTACGACACGAGGCCACTCTATTTCCCTTAGCGAC -722

PILC2MS11 - TGGCAGCGCGAAAGTACCGCCATGGCCTATTATCTGGACGCCAAACTGCA -800
            ||| ||||||||  |||||||||||||||||||||||| |||||||||||
PILCA1493 - TGGAAGCGCGAACATACCGCCATGGCCTATTATCTGAACGCCAAACTGCA -772

PILC2MS11 - CCTGCTGGATAAAACACAGATTGAAAATATCGCGCCAGGCAAAACAGTGA -850
            ||||||||| |||| | |||||||| ||||||| | ||||||||||||| 
PILCA1493 - CCTGCTGGACAAAAAGGGATTGAAGATATCGCCCAAGGCAAAACAGTGG -822

PILC2MS11 - ATTTGGGCATCTTGAGACCGCGCGTCGAGGCAAAGGTAAGGCGGAAGTGG -900
            ||||||||| ||||||||||||||||||||| ||||||||||||    ||
PILCA1493 - ATTTGGGCACCTTGAGACCGCGCGTCGAGGCAACGGTAAGGCGGG---GG -869

PILC2MS11 - GATCTGCTAAATTTTTGGGCTAAGTGGGACATTAAAGATACCGGGCAGAT -950
            || ||||||||||||||||||| |||| ||| |||||| ||| ||| || 
PILCA1493 - GAGCTGCTAAATTTTTGGGCTACGTGGAAGATTGAAGATAAAGGGAACAT -919

PILC2MS11 - TCCGGTCAAGCTCGGCC-TGCCGGAAGTCAAAGCAGGCCGCTGCAT-CAA -998
            |   | ||   || |||| ||||||||||||||||  | || |  |  |||
PILCA1493 - TACAGTNCGCCTNGGCCCTGCCGGAAGTCAAAGCAAGNCGGTTCGTACAA -969

PILC2MS11 - CAAACCGAACCCCAATCCCAAATC---AGCCCTTTCGCCGGCACTGACCG -1045
            |||| ||||||||||||||| |     ||||| || || |||||||||||
PILCA1493 - CAAAGCGAACCCCAATCCCAACGCCAAAGCCCCCTCCCCCGCACTGACCG -1019

PILC2MS11 - CCCCCGCGCTGTGGTTCGGCCCTGTGCAAAATGGCAAGGTGCAGATGTAT -1095
            |||||||||||||||||||||  ||||||  | |||| |||| || |||||||
PILCA1493 - CCCCCGCGCTGTGGTTCGGACCTGTGAAAGATGGTAAGGCGGAGATGTAT -1069

PILC2MS11 - TCCGCTTCGGTTTCCACCTACCCCGGCAGCTCGAGCAGCCGCATCTTCCT -1145
            ||||||||||||||| ||||||||| ||| ||||||||||||||| |||
PILCA1493 - TCCGCTTCGGTTTCTACCTACCCCGACAGTTCGAGCAGCCGCATCTACCT -1119

PILC2MS11 - CCAAGAGCTGAAAACTAAAACCGACCCCGCCCGGCCCGGCCGGCATTCCC -1195
            ||| | ||||||||  |||||||||||| |   ||||||| |||||||
PILCA1493 - TCAAAATCTGAAAAGAAAAACCGACCCCGGCAAACCCGGCCGCCATTCCC -1169

PILC2MS11 - TCGCCGCTTTGAATGCGCAGGATATCAAATCCCGCGAGCCGAATTTCAAC -1245
            | |   | ||||| || || | |   ||||| |||  || ||||||||||| |
PILCA1493 - TCGAAACCTTGACTGAGAATGATATTAAAAGTCGAGAGCCGAATTTCACA -1219

PILC2MS11 - TCAAGGCAGACCGTCATCCGATTGCCGGGCGGCGTGTACCAGATCGCCCC -1295
            |||| |||  ||||||||||||    ||||||||  |||||   |   |
PILCA1493 - GGGCGGCAAACCATCATCCGATTGAATGCGGCGTACGTGAGATCAAACT -1269

PILC2MS11 - GG---GCAATAGCGGCCGGGTCGCGGGTTTTAATGGCAATGACGGCAAAA -1342
            ||   | || |     |||||    |||||||||| ||||||||||| |
PILCA1493 - GGATAGAAACAATACTGAGGTCGTCAATTTTAATGGAAATGACGGCAACA -1319

PILC2MS11 - ACGACACTTTCGGCATCTACAAGGACAGGCTCGTCACACCTGAGGTCGGC -1392
            |||||||||||||||   ||||| |    || |||| ||||||   | ||
PILCA1493 - ACGACACTTTCGGCATTGTTAAGGACTTGGGCGTCGAACCTGATACCAGC -1369

PILC2MS11 - GAGTGGAGCGAAGTGCTGCTGCCTTGGACGGCCCGGTATTACGGTAATGA -1442
            |||||||      ||||| ||||||||||||  |||  || |  | ||||
PILCA1493 - GAGTGGAAAAAAGTATTGCTGCCTTGGACGGTTCGGGGTTTTGCTGATGA -1419
```

Fig. 4C.3

```
PILC2MS11 - CGATATATTTAAAACATTCAACCAACCAAACAGCAAAACACAAAACGGCA -1492
            | ||| |||||||| |||||||| || | | | ||    |  || ||
PILCA1493 - CAATAAATTTAAAGCATTCAACAAAGAAGAAAACA------ACGACAACA -1463

PILC2MS11 - AAAAACAATACAGCCAAAAATACCGCATCCGCACAAAAGAAAATGACAAT -1542
            |  | ||||||||||||||||||||| ||||   ||   | | || | |
PILCA1493 - AGCCAAAATACAGCCAAAAATACCGCAGCCGCGACAACAACAAGGGCGAA -1513

PILC2MS11 - GACAAACCCCGCGATTTGGGCGACATCGTCAACAGCCCGATTGTCGCGGT -1592
            |||   |||||||||||||||||||||||||||||||||| || || |||||
PILCA1493 - ---------CGCAATTTGGGCGACATCGTCAACAGCCCCATCGTGGCGGT -1554

PILC2MS11 - CGGCGGGTATCTGGCAACTTCTGCCAACGACGGGATGGTGCATATCTTCA -1642
            ||||| |||| |||| ||||| ||||||||||||||||||||||||||||
PILCA1493 - CGGCGAGTATTTGGCTACTTCCGCCAACGACGGGATGGTGCATATCTTCA -1604

PILC2MS11 - AAAAACCGGCACGGATGAACGCAGCTACAATCTGAAGCTCAGCTACATC -1692
            || ||| ||||   |||   | |||||||||||||||||||||||||||||
PILCA1493 - AACAAAGCGGCGGGGACAAGCGCAGCTACAATCTGAAGCTCAGCTACATC -1654

PILC2MS11 - CCCGGTACGATGGAGCGTAAGGATATTGAAGGCAATGACTCCGACCTCGC -1742
            || || |||||| ||| |||||||||| || || || ||| ||| ||
PILCA1493 - CCTGGAACGATGCCGCGCAAGGATATTCAAAACACCGAATCCACCCTTGC -1704

PILC2MS11 - CAAAGAGCTGCGCACCTTTGCCGAAAAAGGCTATGTGGGCGACCGCTACG -1792
            ||||||  ||||||||||||||||||||||||||||||||||||||||||
PILCA1493 - CAAAGA-MTGCGCACCTTTGCCGAAAAAGGCTATGTGGGCGACCGCTACG -1753

PILC2MS11 - GCGTGGACGGCGGCTTTGTCTTGCGCCGCATTACAGATGACCAAGACAAG -1842
            ||||||||||||||||||||||||||  ||   ||| || | || |
PILCA1493 - GCGTGGACGGCGGCTTTGTCTTGCGCAAAGTT---GATAACTTAAACGGG -1800

PILC2MS11 - CAAAAACATTTCTTTATGTTTGGTGCGATGGGCCTGGGCGGCAGAGGCGC -1892
            |||| |  |  |||||||| || ||||||||| | ||||| |||||||||
PILCA1493 - SAAAACCGCGTGTTTATGTTCGGCGCGATGGGCTTTGGCGGSAGAGGCGC -1850

PILC2MS11 - GTATGCCTTGGATTTAAGCAAAATCGACAGCAGCAACCTGACCGGCGTTT -1942
            |||||||||||||||| |||| |||| |||| ||| ||||| |||||
PILCA1493 - GTATGCCTTGGATTTGACCAAAGCCGACGGCAGTGACCCGACCGCCGTTT -1900

PILC2MS11 - CCATGTTTGATGTCCAAAACGACAAAAATAACAATAACAATAAGAATGAC -1992
            || ||||||||||              ||  ||||| || |||| |
PILCA1493 - CCCTGTTTGATGT---------------AAAAGATAACGGCAATAATGGC -1935

PILC2MS11 - AATAATCGCGTGAAATTAGGCTACACCGTCGGTACGCCGCAAATCGGCAA -2042
            |||||||||||| |||||||||||||||||||| ||||||||||||| ||
PILCA1493 - AATAATCGCGTGGAATTAGGCTACACCGTCGGCACGCCGCAAATCGGSAA -1985

PILC2MS11 - AACCCAAAACGGCAAATACGCCGCCTTCCTCGCTTCCGGTTATGCGGCTA -2092
            ||||||  ||||||||||||||||||||||||| ||||||||||| |||
PILCA1493 - AACCCACGACGGCAAATACGCCGCCTTCCTCGCCTCCGGTTATGCGACTA -2035

PILC2MS11 - AAAA---TATTGGCAGCGGCGATAATACAACCGCGCTGTATGTGTATGAT -2139
            || |   |||| |||||||||| |||| ||||||||||||||||||||||
PILCA1493 - AAGAAATTATTACCAGCGGCGACAATAAAACCGCGCTGTATGTGTATGAT -2085

PILC2MS11 - TTGGAAAACACCAGTGG---TAGTCTGATTAAAAAAATCGAAGCACCCGG -2186
            ||||||  | | ||     || ||||||||||||||||||||| ||||||
PILCA1493 - TTGGAAGGAAACGGTACGAATAATCTGATTAAAAAAATCGAAGTACCCGG -2135
```

Fig. 4C.4

```
PILC2MS11 - CGGCAAAGGCGGGCTTTCGTCCCCCACGCTGGTGGATAAAGATTTGGACG -2236
            ||||||  ||||||||||||||||||||||||||||||||||||||||||
PILCA1493 - CGGCAAGGGCGGGCTTTCGTCCCCCACGCTGGTGGATAAAGATTTGGACG -2185

PILC2MS11 - GCACGGTCGATATCGCCTATGCCGGCGACCGGGGCGGCAATATGTACCGC -2286
            |||||||||||||||||||||||||||| || ||||| ||||||||||||
PILCA1493 - GCACGGTCGATATCGCCTATGCCGGCGATCGCGGCGGGAATATGTACCGC -2235

PILC2MS11 - TTTGATTTGAGCAATTCCGATTCTAGTAAATGGTCTGCAAAGGTTATTTT -2336
            |||||||||||| |   ||| ||       ||||||||| |    ||||||
PILCA1493 - TTTGATTTGAGCAGTCAAGATCCTCAACAATGGTCTGTACGCACTATTTT -2285

PILC2MS11 - CGAAGGCG-ACAAGCCGATTACCTCCGCGCCCGCCGTTTCCCGACTGGCA -2385
            ||||||  |  || |||||||| ||||||||||||||   |||
PILCA1493 - TGAAGGCACAAAACCCGATTACTTCCGCGCCCGCTATTT           -2324
```

RECOMBINANT PILC PROTEINS, METHODS FOR PRODUCING THEM AND THEIR USE

This application claims priority under 35 USC 119 to P 4,336,530.2 Fed. Rep. of Germany, filed Oct. 26, 1993, and PCT/EP94/03494, filed Oct. 25, 1994.

The invention relates to recombinant gene sequences for synthesizing a protein having the biological activity of the PilC protein. Furthermore, the invention relates to DNA recombinant methods for the production of proteins having the biological activity of the PilC protein as well as the molecular-biological tools required therefor. In addition, the invention relates to proteins having the biological activity of the PilC protein and its antibodies. Other embodiments of the invention are pharmaceutical compositions comprising the mentioned proteins or antibodies. Preferably, these pharmaceutical compositions serve as vaccines for the immunization against pathogenic bacteria bearing type 4 pili. The invention also relates to kits for the detection of bacteria bearing type 4 pili or antibodies directed against them comprising the mentioned proteins or antibodies. Finally, the invention relates to cellular receptors for bacteria bearing type 4 pili and analogues thereof.

A crucial step in the occurrence and the manifestation of any infection is the attachment of the pathogen to certain molecular structures (receptors) of the host organism. The pathogen's structures responsible for attachment shall be referred to as adhesins. It is possible that multiple molecular interactions between adhesins of the pathogen and receptors of the host organism are necessary for the occurrence and/or the manifestation of an infection. On the other hand, it is thinkable that blocking one single molecular interaction between an important adhesin and a receptor is sufficient to prevent an infection. Blocking molecular adhesin-receptor interactions is a possible form of prevention and/or therapy of infectious conditions. Prophylactic approaches include, for instance, the formation of antibodies directed specifically against the adhesin and block any interaction with its receptor by active immunization (vaccination). However, the interaction may principally also be prevented in the sense of a prophylactic or therapeutic measure by passively administered antibodies or other substances, for instance adhesin or receptor analogous substances, which shall be referred to under the generic term inhibitors. Important adhesins of numerous gram negative pathogens are pili (also termed fimbriae or fibrillae). They are polymeric structures forming fine thread-like appendages to the surface of the bacteria. Pili make it possible for the bacteria to attach to specific receptors of the host organism via the adhesins contained in the pili. In some cases it was shown that the loss of the pili leads to the pathogen's loss of infectiousness. This loss of infectiousness can be explained by the loss of the capability to form attachments. Therefore, blocking the molecular interaction between pilus adhesin and receptor can avoid or stop the infection of the host organism.

In gram negative bacteria, different types of pili are known. The majority of all known pili are heteropolymeric structures comprising several subunits, one main subunit and other inferior subunits which are present in only a few copies. In some well examined cases the inferior subunits are the actual adhesive structures (adhesins), whereas the main subunit which is present in a high number of copies takes over the function of a framework (Lindberg et al., Nature 328, 84–87, 1987). Numerous pathogenic gram negative bacteria species form type 4 pili, which are also referred to as N-Me-Phe or type IV pili. They include the pathogenic Neisseria species *N. gonorrhoeae* and *N. meningitidis*, causing gonorrhoe and bacterial meningitis, respectively, in humans. However, there is no effective vaccine against *N. gonorrhoeae* so far. The capsula-specific vaccines against some sero groups of *N. meningitidis*, however, are available; unfortunately they offer only partial protection and are considered immunologically problematical. Thus, these infections are usually treated with antibiotics; however, the ever increasing resistance of the pathogens to antibiotics causes problems. The development of alternative methods of treatment is therefore urgent. Another important pathogen forming type 4 pili in humans is *Pseudomonas aeruginosa* (Sastry et al., FEBS Letters 151, 253–255, 1983), which is a central problem for patients suffering from cystic fibrosis, immunodeficiencies and in connection with septic infections. Effective vaccines and/or inhibitors of this pathogen are not yet available; problematic is above all the increased spreading of multi-resistant strains. Alternative methods of treatment are thus urgently required in this field too. More examples of important pathogens forming type 4 pili are enteropathogenic *Escherichia coli* (EPEC; Giron et al., Science 254, 710–713, 1991), *Vibrio cholerae* (Shaw et al., Infect. Immun. 58, 3042–3049, 1990), *Bacteroides nodosus* (McKern et al., FEBS Letters 164, 149–153, 1983), *Moraxella bovis* (Marrs et al., J. Bacteriol. 163, 132–139, 1985) and other pathogens, causing diseases in humans and animals and vaccines against which are searched for intensively. Type 4 pili are defined by the structure of their main subunit, usually referred to as pilin; besides, there are specific terms for the pilin main subunit for individual species of bacteria, e.g. PilE for *N. gonorrhoeae* or PilA for *Pseudomonas aeruginosa*. The pilin's structure of the type 4 pili differs substantially from that of main subunits of other pilus types, such as the group of pap-like pili (Baga et al. J. Bacteriol. 157, 330–333, 1984). Characteristics of the pilin of type 4 pili are (a) the short, positively charged, aminoterminal signal sequence of the pilin's preform (exception *V. cholerae* type 4 pilin), (b) the hydrophobic amino terminal region of the mature pilin that exhibits strong sequence homology between different type 4 pilins, (c) the modification of the amino terminal Phe residue of the mature pilin by means of a methyl group in N position (N-Me-Phe), (d) two Cys residues in the carboxy terminal region of the pilin that form a loop and (e) a property termed twitching motility.

So far, PilC proteins were detected as components of N. gonorrhoeae and *N. meningitidis*. Up to now, an assembly function in the pilus biogenesis was considered to be a function of these PilC proteins (Jonsson, Dissertation, New Series No. 322, University of Umea, ISSN 0346-6612). However, these works never indicated a possible role as an important adhesin. In other tests, scientists succeeded in isolating mutants of *N. gonorrhoeae* which did still form pili but no longer exhibited an adherence to epithelial cells (Rudel et al., Mol. Microbiol. 6, 3439–3450, 1992). These mutants turned out to be phase-variant strains that had stopped forming PilC proteins. A direct function of the Neisseria PilC proteins could not be derived from these experiments. However, the experiments showed that the assembly of the Neisseria pili can take place also if no PilC proteins are present. Scientists had been successful in cloning a single PilC-protein encoding gene in *E. coli*. This was achieved by means of the gel electrophoretic purification of PilC protein from isolated Neisseria pili (Jonsson et al., EMBO J. 10, 477–488, 1991). The gel electrophoretically purified PilC protein was used for the recovery of antiserum. The gel electrophoretically purified PilC protein had no biological activity in the sense of this invention. The corresponding antiserum thus does not have the property of this invention to block the attachment of piliated Neisseria to epithelial cells. Using the antiserum, scientists at first succeeded in identifying an *E. coli* phage clone carrying a partial PilC-encoding gene. An *E. coli* clone with an intact PilC-encoding gene could be identified by means of the partial PilC-encoding gene using DNA hybridization (Jonsson et al. EMBO J. 10, 477–488, 1991). This recombinant PilC-encoding gene was translationally inactive due to its variable, homopolymeric sequence so that a synthesis of biologically active PilC protein did not take place. The nucleotide sequence of this first PilC-encoding gene (pilcl) from the *N. gonorrhoeae* MS11 strain is known; a partial sequence of a second gene (pilC2) from this strain is known as well (Jonsson et al., EMBO J. 10, 477–488, 1991; Jonsson, Dissertation, New Series No. 322, University of Umea, ISSN 0346-6612). However, none of these genes has made it possible to produce PilC.

Thus, the invention essentially is to solve the technical problem to provide biologically active proteins having the biological activity of the PilC protein. This technical problems is solved by providing the embodiments characterized in the claims.

Thus, the invention relates to recombinant gene sequences for synthesizing a protein having the biological activity of the PilC protein, whose sequence portion encoding the phase-variable signal peptide and containing a homopolymeric nucleotide sequence is characterized by the two following modifications:

(a) modification of the homopolymeric nucleotide sequence to form an invariable heteropolymeric nucleotide sequence or (b) substitution of the phase-variable signal-peptide encoding sequence portion against another, non-phase-variable nucleotide sequence that encodes a signal peptide compatible with the secretion of the PilC protein so that the expression of the recombinant gene sequence in a host cell is made possible unaffected by phase variations.

These DNA-sequences of this invention serve for the expression of proteins having the biological activity of the PilC protein. In this invention, the term "biological activity of the PilC protein" relates to the encoded protein's capability to support the assembly of type 4 pili, to mediate the attachment of bacteria bearing type 4 pili to cellular receptors or to the immunological suitability for the induction of antibodies for bacteria bearing type 4 pili, which compete with the attachment of the bacteria to their cellular receptors and preferably block the attachment. According to this invention, the term "protein" relates to naturally occurring proteins or to modifications or fragments thereof exhibiting the above-mentioned biological activity. The term "PATHOGENIC BACTERIA BEARING TYPE 4 PILI" as used in this invention refers to bacteria that, on the one hand, are in a causal relationship with the pathogenesis of diseases and, on the other hand, as an essential element of their pathogenic property, form type 4 pili, which are necessary for the attachment of the bacteria to cellular receptors in the infected host organism.

"HOMOPOLYMERS" are nucleotide sequences consisting of a sequence of identical nucleotides (e.g. 5'-CCCCCCC-3'). In this invention, "HOMOPOLYMERIC NUCLEOTIDE SEQUENCES" are defined by their property to spontaneously or inducedly add one or several identical nucleotides to the existing homopolymeric nucleotide sequence or lose the same therefrom. The addition and/or loss of identical nucleotides in homopolymeric nucleotide sequences results in a "PHASE VARIATION". This phase variation is caused by a RecA-protein independent process, which takes place substantially spontaneously (Robertson & Meyer, Trends Genet. 8, 422–427, 1992). The changes in the nucleotide sequence underlying the phase variation effect the translational reading frame of a gene and therefore the formation of the intact gene product. In the sense of this invention phase variation is undesired because under the control of a strong promoter, phase variation of the PilC encoding DNA will cause a changed reading frame and thus a loss of the formation of the desired protein having the biological activity of the PilC protein. An "INVARIABLE HETEROPOLYMERIC NUCLEOTIDE SEQUENCE" in the sense of this invention is therefore a nucleotide sequence derived from a homopolymeric nucleotide sequence by addition or exchange of non-identical nucleotides (i.e. in the case of the sequence 5'-GGGGGGGGGGGGGG-3' (SEQ. ID NO.:4) the nucleotides A, C and/or T) and, due to these modifications, has become "NON PHASE-VARIABLE", i.e. exhibits no phase variations. Due to the genetic code, it is possible to modify the homopolymeric nucleotide sequence such that the encoded amino acid sequence either remains unchanged or is also changed.

A "SIGNAL PEPTIDE" as used in this invention is an amino acid sequence at the amino terminus of the preform of a protein secreted from gram negative bacteria. A signal peptide makes the secretion of a protein via the general export path of the internal bacteria membrane possible (Pugsley, Microbiol. Rev. 57, 50–108, 1993). The phase-variable signal-peptide encoding portion of the gene sequence of this invention is modified (a) by modification of its homopolymeric nucleotide sequence (see above) or (b) by substitution of the phase-variable signal-peptide encoding portion, which, due to the comprised homopolymeric nucleotide sequence phase, is variable. The substitution is a partial or a complete exchange of the signal-peptide encoding sequence portion by another signal-peptide encoding sequence that makes the secretion of the PilC protein via the mentioned general export path possible, contains no phase-variable homopolymeric nucleotide sequence and is altogether a non-phase-variable nucleotide sequence. The changes (modification or substitution) are carried out with the aim to make the expression of the gene sequence in a host cell possible without any influences by phase variations in order to guarantee the formation of PilC protein under stable conditions and in large amounts (production of surplus). Hybridization of chromosomal DNA of, for instance, *N. gonorrhoeae* with a complete pilC gene as a probe indicate that two related pilC genes exist in the chromosome of this species. However, if subgenic fragments of a pilC gene are used as a probe, more cross hybridizing genes can be rendered visible that are also pilC genes which, however, are only in a distant relationship. The detection of such distantly related pilC genes is based on the cross-hybridization of constant regions of the DNA sequence between two or more related pilC genes. Constant regions of the DNA sequence can be defined by means of a sequence comparison between two related genes. The definition of constant regions of the DNA sequence thus results in the possibility to identify also distantly related pilC genes. The repeated sequence comparison with such a distantly related gene, in turn, results in new constant regions of the DNA sequence which, again, can be used for the identification of pilC genes, etc. This way, all members of the pilC gene family within and outside a bacteria species can gradually be detected.

The recombinant gene sequences of this invention render the production of proteins having the biological activity of the PilC protein in considerable amounts possible. This also makes the general identification of inferior subunits of the type 4 pili and their reliable characterization as adhesins possible. The invention allows in particular for the detection of the PilC proteins of pathogenic Neisseria (*N. gonorrhoeae* and *N. meningitidis*) in their function as important adhesins. Furthermore, the invention allows for the detection of PilC analogous proteins of other bacteria species forming type 4 pili. The detection according to this invention of the adhesin function of an inferior subunit of a type 4 pilus and/or PilC analogous proteins has not been described so far for any bacteria species producing type 4 pili. The term "PilC analogous protein" relates exclusively to the structural relationship (of nucleotide and amino acid sequence) with the PilC proteins of the pathogenic Neisseria and to the analogous function with the Neisseria PilC proteins as receptor binding adhesins. The PilC analogous proteins of other bacteria species forming type 4 pili of this invention are not necessarily identical with or related to the proteins referred to as PilC in literature (for instance the known PilC protein of *Pseudomonas aeruginosa* (Nunn et al., J. Bacteriol. 172, 2911–2919, 1990) is not a PilC analogous protein of this invention).

The main subunit of the type 4 pili was erroneously considered an important adhesin in some cases (Rothbard et al., PNAS (USA) 82, 919, 1985; Paranchych, In: The Bacteria Vol. XI, Molecular Basis of Bacterial Pathogenesis, Academic Press, 61–78, 1990 and citations therein). Based on these findings and/or hypotheses, numerous attempts have been made to block the adherence of bacteria to human or animal cells using antibodies and/or adherence blockers or to stop a bacterial infection by means of vaccination using the type 4 pilus main subunit. Despite partial success (Paranchych, In: The Bacteria Vol. XI, Molecular Basis of Bacterial Pathogenesis, Academic Press, 61–78, 1990 and citations therein; Tramont, Clin. Microbiol. Rev. 2, 74–77, 1989 and citations therein) it has not yet been possible to develop a widely effective vaccine or a widely effective inhibitor based on the main subunit of the type 4 pili. There are two possible explanations: (a) The main subunit of a type 4 pilus comprises no important adherence functions so that the attachment of the pili to the receptor is not blocked and/or (b) the vaccines or the inhibitor are not effective or not widely enough effective due to the structural variability of the pilin main subunit.

The latter explanation relates to the assumption that a vaccine directed against pilin might cause a complete loss of the pili's capability to adhere, independent of whether or not pilin is an adhesin. The effect of the antibodies directed against pilin might affect the structure function of the pilin and thus indirectly the adherence properties of the pili altogether. That this way obviously does not lead to success (Johnson et al., J. Infect. Dis. 163, 128–134, 1991) is mainly due to the mentioned structural variability of the pilin. It is known that pilin of bacteria species forming type 4 pilus exhibits inter-strain specific and/or intra-strain specific structural variability. This structural variability is the reason for an indirect blocking of the adherence by means of antibodies directed against the variable main pili subunit not being widely effective but rather being restricted to that certain strain or the variant. This is why it has been impossible to develop a widely effective vaccine on the basis of the pili main subunit (pilin).

The PilC proteins that can now be produced using the gene sequences of this invention, e.g. those of pathogenic Neisseria, also show structural variability, as can be seen, for instance, from the comparison of the encoding nucleotide sequences (FIG. 4, SEQ. I.D. Nos. 1–3). Contrary to the variability of the pilins, however, the variability of the PilC adhesins is markedly less and has no (or negligible) effect on the function of the PilC proteins, namely the molecular interaction with the receptor. This statement is supported by the competition experiments with biologically active PilC protein (Tab. 2) since bacteria forming different pilin molecules and/or PilC proteins can be displaced using the same PilC protein. Thus, although PilC proteins varying in structure are formed within one species, these PilC proteins of one species recognize the same or only a few different receptors in the host organism. It is therefore possible to develop a widely effective vaccine and/or widely effective adherence inhibitors based on only a few variant forms of the PilC proteins of one species. In addition, this invention makes it possible to develop widely effective receptor analogues based on only one or a few receptors. These possibilities also apply to the PilC-analogous adhesins formed by bacteria forming type 4 pili that do not belong to the species Neisseria. It may be assumed that the cell, tissue and host tropism of a species is largely determined by the interaction of the adhesins with their corresponding cellular receptors. These tropisms are very marked in many pathogens, particularly also in bacteria forming type 4 pilus. From this fact it can be inferred that also the PilC analogous adhesins of this invention of one species with their defined tropisms interact only with one or a few cell, tissue and host specific receptors. This involves the possibility to develop widely effective vaccines and other inhibitors of an infection corresponding to the use of the PilC adhesins of the Neisseria based on the PilC analogous adhesins of other species and/or their receptors. One important aspect of the present invention was to detect the function of the PilC proteins as important adhesins in connection with the occurrence of an infection. In order to do so, it was necessary to recover biologically active PilC protein in pure form and to prove its biological activity in suitable test systems.

For producing a recombinant gene sequence of this invention the complete pilC2 gene from the *N. gonorrhoeae* MS11 strain was isolated based on the information available on PilC1 and its gene and cloned into *E. coli*. In order to produce the protein of this invention having the biological activity of a PilC protein of the genus Neisseria from this gene, the phase-variable, signal-peptide encoding, homopolymeric sequence portion of the pilC2 genes was modified such that the expression of the recombinant genes in a host cell is rendered possible unaffected by phase variation. This was achieved by modification of the homopolymeric sequence portion to form a heteropolymeric sequence using suitable oligo nucleotides by means of the polymerase chain reaction (PCR) (Example 2).

In a preferred embodiment, the gene sequence of this invention can be obtained by modification of a DNA sequence stemming from a pathogenic bacterium bearing type 4 pili. This bacteria group was characterized in detail above. Examples of such bacteria are Neisseria, particularly *N. gonorrhoeae* and *N. meningitidis,* pseudomonades, particularly *P. aeruginosa,* enteropathogenic Escherichia, particularly *E. coli* (EPEC), *Vibrio cholerae, Bacteroides nodosus* and *Moraxella bovis.*

In a more preferred embodiment of this invention, the gene sequence is obtained by modification of a DNA sequence from a bacterium of the genus Neisseria, preferably *Neisseria gonorrhoeae* or *Neisseria meningitidis.*

The gene sequences of the *N. gonorrhoeae* pilC2 gene (SEQ. ID. NO.:1) and of the *N. meningitidis* pilC A1493 (SEQ. ID. NO.:2) gene shown in FIG. 4 of this invention are especially preferred. The shown sequences start at position 1 with the codon ATG coding for the first amino acid (Met). The region coding for the signal peptide stretches from positions 1 to 99 based on gene pilC2. The phase-variable homopolymeric sequence portion is contained therein, stretching from positions 79 to 91. The constant nucleotides of the shown sequences are marked with asterisks. Individual constant sequence portions of the genes pilC1 and pilC2 are separately shown in Table 3.

DNA hybridization experiments with the complete pilC1 gene, with fragments of the pilC1gene obtained by means of restriction endonucleases, or with the previously known gene portion of the pilC2 gene of *N. gonorrhoeae* MS11, indicated the existence of 2 (Jonsson et al., EMBO J. 10, 477–488, 1991) and/or maximal 3 (Bihlmaier et al., Mol. Microbiol. 5, 2529–2539, 1991) related pilC genes within this strain. The determination of the nucleotide sequence of the second complete pilC gene of this invention (pilC2) and the comparison of the two pilC nucleotide sequences (FIG. 4, SEQ. ID. NOs.:1–3) make it possible according to this invention to determine preserved regions of the pilC genes (Table 3). Corresponding subgenic, preserved fragments and/or oligo nucleotides of a pilC gene can then, unlike complete genes and/or larger gene fragments, be used as hybridization probes due to their corresponding homologies to the genes related to preserved nucleotide sequences in order to identify and isolate such related genes altogether. Thus, the gene sequence of this invention is available in another embodiment by modification of a DNA sequence that hybridizes to a constant region of the DNA sequence of FIG. 4, SEQ. I.D. NOs. 1–3, and/or Table 3 and codes for a protein having the biological activity of the PilC protein.

Another subject-matter of the invention are thus gene sequences that hybridize to a constant region of the gene sequence shown in FIG. 4, SEQ. I.D. NOs. 1–3, and/or Table 3, code for a protein having the biological activity of the Pilc protein and stem from a pathogenic bacterium bearing type 4 pili that is not of the genus Neisseria.

According to this invention the length of a homopolymeric nucleotide sequence modified to form a heteropolymeric nucleotide sequence amounts to 5 or more nucleotides. The sequence examples given in FIG. 4 (SEQ. I.D. NOs. 1–3) are 12 G (pilC1), 13 G (pilC2), 9 G (pilC A1493); cf. position 79 to position 91 based on the gene sequence pilC2.

In another preferred embodiment of this invention, the modified gene sequence codes for a protein having the biological activity of the PilC protein and exhibiting an oligo histidine portion suitable for its purification. This oligo histidine portion preferably contains 6 histidine residues (His$_6$). The presence of the His$_6$ peptide makes it possible to selectively bind the PilC protein of this invention to a nickel-NTA (Ni-nitrilo triacetic acid)-agarose column (Hochuli et al., J. Chromat. 411, 177–184, 1987; Hochuli et al., Bio/Techno. 6, 1321–1325, 1988) with the eluted protein being pure PilC protein.

In a more preferred embodiment of this invention, the oligo histidine region is at the N terminus or the C terminus of the mature form of the encoded proteins. This ensures a spatial structure less liable to disturbances of the proteins.

In another embodiment, the invention relates to recombinant vectors that comprise a gene sequence of this invention. Examples of such vectors are vectors pBR322 and pBA which replicate in *E. coli*, vectors based on the bacteriophages M13, fd or lambda, broad host range vectors, shuttle vectors that correspond to Hermes vectors (Kupsch et al., filed for publication) which make it possible to incorporate cloned genes into the DNA of the recipient Neisseria cell as well as the plasmid ptetM25.2, which can be used for the conjugative transfer of genes between Neisseria (Kupsch et al., filed for publication).

In a preferred embodiment of the vectors of this invention, the mentioned gene sequence is controlled by a promoter. Examples of suitable promoters according to this invention are promoters that are functional in gram negative bacteria and, in particular, inducible promoters. In an especially preferred embodiment of this invention, the promoter is Ptrc, which can be repressed in Neisseria and *E. coli* as well as induced in the presence of IPTG in the presence of an expressed lacI$^q$ gene.

In another embodiment, the invention relates to host cells that comprise one or several recombinant vectors of this invention. The host cells of this invention serve for replication, transcription and translation of the gene sequence of this invention for the synthesis of a protein having the biological activity of the PilC protein. They are preferably gram negative bacteria which render it possible to secrete the synthesized protein via the inner membrane and fold it correctly. Examples of such host cells are *E. coli* K12 and other gram negative bacteria, for which suitable cloning vectors are available. Preferably, the host cell of this invention is a non-piliated Neisseria strain, which—like *N. gonorrhoeae* N174—has lost its capability to form its pili due to a defective pilE gene. The pilE gene codes for the main subunit (pilin) of the Neisseria pili. Due to the defective pilE gene, no pilin is synthesized making the recovery of biologically active PilC protein absolutely free of pilin possible.

In another embodiment, the invention relates to methods for the production of a substantially pure protein having the biological activity of the PilC protein, comprising culturing a host cell of this invention under suitable conditions and purifying the protein.

In a preferred embodiment of the production method of this invention, the purification of the protein having the biological activity of the PilC protein takes place by means of an affinity chromatography, preferably an affinity chromatography, wherein the oligo histidine portions contained in the protein of this invention are used for attachment of the proteins.

In another embodiment, the invention relates to substantially pure protein having the biological activity of the PilC protein obtainable according to the described methods of this invention. Furthermore, the invention relates to substantially pure protein having the biological activity of the PilC protein encoded by a gene sequence of this invention. The proteins having the biological activity of the PilC protein of this invention considerably differ from the state of the art in that they are biologically active, whereas PilC proteins known from the state of the art could not be provided in biologically active form. The PilC protein of this invention exhibits high purity and is particularly free of pilin. Besides, the proteins having the biological activity of the PilC protein of this invention can be produced in amounts large enough for instance for the production of vaccines. This was not possible with traditional production and purification methods. Depending on the expression system the proteins having the biological activity of the PilC protein obtainable according to this invention differ also structurally from the known PilC proteins, which are not biologically active. Recombinant PilC proteins for instance may be marked by additional, deleted, inverted or otherwise modified amino acid sequences.

In another embodiment, the protein having the biological activity of the PilC protein of this invention is marked such that it can be detected by common methods. Examples of such markers in recombinant PilC proteins are amino acid sequences that can be identified by means of known biological and chemical methods. A biological method e.g. relates to sequences that can be detected by means of an antibody; a chemical method e.g. relates to sequences that can be detected by the formation of an Ni-NTA complex.

In another embodiment, the invention relates to antibodies to proteins having the biological activity of the PilC protein of this invention, wherein the antibodies inhibit attachment of the protein to the corresponding receptor. These antibodies of the invention are monoclonal or polyclonal antibodies. The invention also relates to common fragments of these antibodies, e.g. $F_{ab}$ or $F_{(ab)2}$ fragments. Furthermore, the invention relates to antibodies having the mentioned attachment activity that can be produced by recombinant methods as well as for instance bivalent antibodies. Furthermore, the invention relates to anti-idiotypical antibodies having the attachment activity of the PilC protein to cellular receptors or the immunological activity of the PilC protein for the induction of antibodies to bacteria bearing type 4 pili that inhibit attachment of the protein to the corresponding receptor.

In another embodiment, the invention relates to pharmaceutical compositions comprising a protein of this invention or an antibody of this invention, optionally in combination with a pharmaceutically acceptable carrier. Preferably the pharmaceutical compositions of this invention are vaccines, more preferably vaccines for the immunization against pathogenic bacteria bearing type 4 pili. Most preferably they are vaccines against bacteria of the genus Neisseria, preferably Neisseria gonorrhoeae or Neisseria meningitidis. These pharmaceutical compositions make a reliable prevention of gonorrhoe or meningitis possible. The surprising usability of the proteins having the biological activity of the PilC protein of this invention for these medical indications is due to the novel finding of this invention that the PilC proteins are the adhesins of the pathogenic bacteria bearing type 4 pili and not, as erroneously assumed in the state of the art, the pilin main subunits, such as PilE in N. gonorrhoeae.

Furthermore, the invention relates to kits for the detection of bacteria bearing type 4 pili or antibodies directed against them comprising a protein of this invention or an antibody of this invention. Preferably these kits are suitable for the detection of bacteria of the genus Neisseria, preferably Neisseria gonorrhoeae or Neisseria meningitidis. Examples of the detection processes that may be carried out using the kits of this invention are radio immuno assays or ELISAs (enzyme-linked immuno assays).

In another embodiment, the invention relates to cellular receptors for bacteria bearing type 4 pili that have the capability to attach to a protein of this invention. Such receptors may be isolated and identified by means of the proteins of this invention. This way, it is possible to couple a PilC protein to a matrix and to purify the receptor by means of affinity chromatography at the attached PilC protein and maintain the receptor in a pure form. With the purified receptor of this invention and the PilC protein of this invention, it is possible to study the physico-chemical interaction between the two purified component and to draw conclusions regarding the type of interaction. The two purified components particularly serve to search for inhibitors of the interaction between PilC protein and its receptor. These inhibitors at the same inhibit the corresponding bacterial infections. Examples of such inhibitors are synthetic peptides or other chemical substances that represent the structure and attachment properties of the adhesins (of the PilC and/or PilC analogous proteins) or of the receptors. The latter are receptor analogues. With the PilC protein of this invention it is also possible to identify the corresponding receptor genetically. For instance, animal/human cells that do not form the receptor can be transfected with the cDNA of cells that do form the receptor. From transfected cells, which now do form the receptor, the cDNA coding for the receptor may be isolated, and by means of the structural analysis of the cDNA, the structure of the receptor of this invention can be recognized. The structure of the receptor of this invention provides information on the predetermined recovery of inhibitors by means of known geneticengineering or chemical methods. Besides, the isolation of the cDNA of the receptors makes it possible to obtain the receptor by means of genetic-engineering methods. In a preferred embodiment, the receptor stems from pathogenic Neisseria.

Figure 1B:
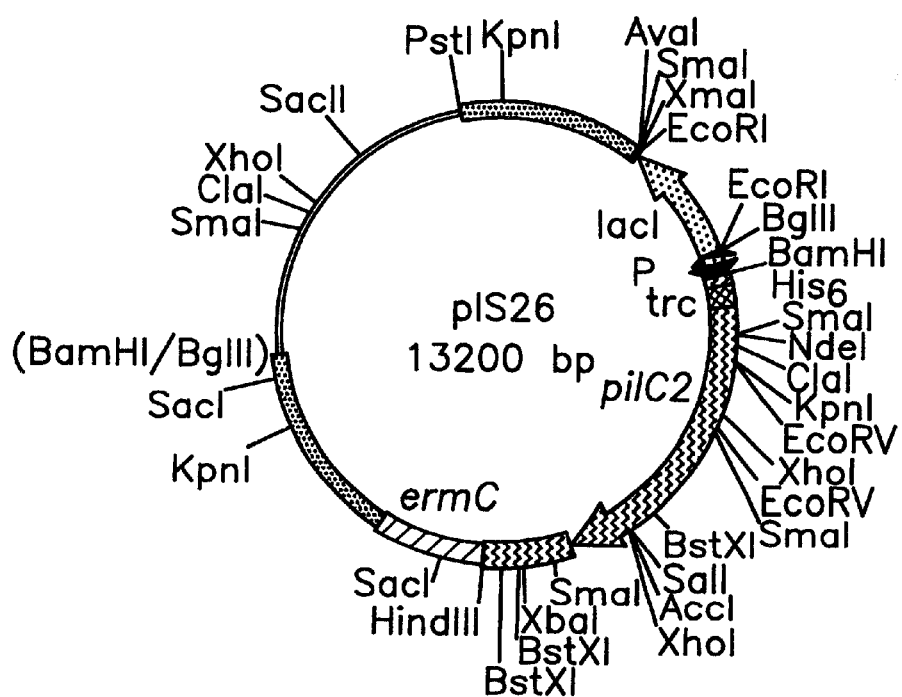

The Figures show:

FIG. 1: Restrictions maps of the plasmids pTR27 (FIG. 1A) and pIS26 (FIG. 1B). Plasmid pTR27 comprises the natural pilC2 gene of the N. gonorrhoeae strains MS11-N133. Starting from this plasmid, a gene sequence of this invention was created in several steps (Example 2; FIG. 2), which sequence is present in cloned form in the plasmid pIS26. Plasmid pIS26 is a Hermes construct (Kupsch et al., filed for publication), which makes both possible the replication in E. coli and the insertion of the recombinant gene sequence of this invention into the conjugative ptetM25.2 plasmid in N. gonorrhoeae. This insertion takes place by transferring the gene sequence contained in the shuttle box by means of double homologous recombination in the two dotted regions of pIS26 with ptetM25.2.

FIG. 2: Construction scheme of the recombinant gene sequence for synthesizing the PilC protein of this invention. The description of the work carried out can be found in Example 2. The DNA region shown in this Figure corresponds to the 5'-terminal region of the pilC2 genes contained in pTR27 (cf. FIG. 1). The terms "TR . . . " refer to the used oligo nucleotides (Example 2). (A) Modification of the phase-variable signal-peptide encoding sequence portion containing a homopolymeric nucleotide sequence. (B) Insertion of a $His_6$-peptide encoding nucleotide sequence. (C) Explanations regarding (A and B) (SEQ. I.D. NOs. 33–40).

FIG. 3: Analytical gel electrophoresis of purified pili of the N. gonorrhoeae wild-type strain N137 (1) and the PilC negative N. gonorrhoeae double mutant N474 (2), as well as of the biologically active PilC2 protein of this invention (3). The isolation of the pili is carried out according to Jonsson et al. (1991); the recovery of the PilC2 protein of this invention is described in Example 3.

FIG. 4: (SEQ. I.D. NOs. 1–3). Nucleotide sequences of the natural pilC gene. (A) Comparison of the nucleotide sequences of the genes pilC1 and pilC2 of Neisseria gonorrhoeae MS11-N133; (B) Comparison of the nucleotide sequences of the pilC1 genes of Neisseria gonorrhoeae MS11-N133 with the partial gene sequence of a pilC gene of Neisseria meningitidis A1493; (C) Comparison of the nucleotide sequence of the pilC2 gene of Neisseria gonorrhoeae MS11-N133 with the partial gene sequence of a pilC genes of Neisseria meningitidis A1493. Examples preserved regions of this invention are marked by asterisks. The modifications carried out for the construction of the recombinant gene sequence of this invention are shown in FIG. 2.

The examples explain the invention in more detail.

EXAMPLE 1

Isolation of the pilC2 Genes of N. gonorrhoeae

Based on the partial sequences of pilC1 and pilC2 published by Jonsson et al. (EMBO J. 10; 477–488, 1991), specific oligo nucleotide probes were constructed (for pilC1: CG31 CGATGGCGCAAACCCATCAA (SEQ. ID. NO.:5); for pilC2: CG32 CGCAGGCGCAAACCCGTAAA) (SEQ. ID. NO.:6), by means of which both pilC genes could be isolated from a plasmid gene bank of genomic DNA of Neisseria gonorrhoeae MS11. For this purpose both probes were radioactively marked using DNA kinase at the 5' end and hybridized against approx. 30000 clones of the gene bank. The positive clones were isolated, again hybridized against the radioactively marked probes and finally characterized. One of the obtained plasmids (pTR27, cf. FIG. 1) contained the entire pilC2 gene, however lacking the promoter for synthesizing the PilC protein. The pTR27 is the basic construct for the determination of the DNA sequence of the pilC2 gene and for the modification of the DNA and protein sequences using genetic engineering methods (cf. Example 2 and Example 6).

EXAMPLE 2

Construction of a N. gonorrhoeae Strain Producing a Surplus of PilC Protein

The modification of the homopolymeric nucleotide sequence, which consisted of 13 G-nucleotides in the case of the cloned pilC2 gene, was achieved in two steps by predetermined mutagenesis by means of the polymerase chain reaction (PCR). In these reactions, the plasmid pTR27 (cf. Example 1, FIG. 1) served as template. The first step (first PCR) comprised two separate PCR reactions of the pilC2 genes having the primer pairs TR12 (TTGGATCCGACGTCCGAAAAGGAAATACGATG, SEQ. ID. NO.:1) and TR28 (GCTCCACCACCTCCGCCGGTATGGGAAAAC, SEQ. ID. NO.:8), as well as TR27 (ACCGGCGGAGGTGGTGGAGCGCAGGCGCAAA CCCGT, SEQ. ID. NO.:9) and TR23 (TGTGTCTCTGCATATGACG, SEQ. ID. NO.:10) (FIG. 1). The PCR reactions (25 cycles of 1 minute at 94° C., 2 minutes at 50° C. and 1 minute at 72° C., each) were carried out in a Perkin Elmer Cetus Thermal Cycler and contained 100 pmole primer, approx. 1 ng pTR27 and 2 units VentR™ polymerase (New England Biolabs) in a volume of 100 µl, each. The oligo nucleotide TR28 hybridized directly before, the oligo nucleotide TR27 directly after the homopolymeric nucleotide sequence region, which resulted in neither the first nor the second PCR fragment containing the homopolymeric nucleotide sequence region. Instead, due to the 5' extensions of the oligo nucleotides TR28 and TR27, fragments 1 and 2 contained an invariable, heteropolymeric nucleotide sequence that codes for the same amino acids as the original homopolymeric nucleotide sequence. Fragments 1 and 2 of the first PCR were separated by means of agarose gel electrophoresis and extracted using GENECLEAN (BIO 101). The purified fragments were merged in the second PCR reaction to form a fragment by now amplifying the oligo nucleotides TR12 and TR23 in a reaction (FIG. 2). The conditions of the second PCR were selected as follows: 100 pmole primer, fragment 1 and fragment 2 in equimolar amounts (50 ng each) and 2 units of the VentR™ polymerase. Unlike during the first PCR, during the second PCR 15 cycles were carried out under the same conditions. The correct exchange of an invariable, heteropolymeric nucleotide sequence for the variable homopolymeric nucleotide sequence was checked by an analysis of the DNA sequence. The obtained PCR product was replaced as a BamHI/NdeI digested fragment by the corresponding BamHI/NdeI fragment of the pTR27 vector so that plasmid pTR81 was obtained. In order to make purification of the PilC protein by nickel chelate affinity chromatography possible (Hochuli et al., Journal of Chromatography 411, 177–184, 1987; Hochuli et al., Bio/Technology 6, 1321–1325, 1988), the DNA sequence coding for a peptide ($His_6$) comprising six histidine residues was inserted in the pilC gene. Cloning of the DNA sequence encoding $His_6$ was carried out analogously to the above-described technique of controlled PCR mutagenesis (FIG. 1). In the first PCR, the plasmid pTR81 served as template. In separate reactions, the fragment 1 was amplified with the oligo nucleotide pair TR12 and TR71 (GTGATGATGGTGGTGATGGGTTTGCGCCTGC GCTCCA, SEQ. ID. NO.:11) and the fragment 2 with the oligo nucleotide pair TR23 and TR70 (CATCACCACCATCATCACCGTAAATACGCTATTATC, SEQ. ID. NO.:12). The oligo nucleotide TR71 paired with the codon for $Thr_{35}$ starting at the (−) strand; the oligo nucleotide TR70 paired with the codon for $Arg_{36}$ starting at the (+) strand (cf. FIG. 2). Due to their 5' extensions, the two oligo nucleotides coded for the $His_6$ sequence that was inserted between the codons $Thr_{35}$ and $Arg_{36}$ in pilC2 by way of the second PCR (cf. FIG. 2). The BamHI/NdeI digested PCR product of the second PCR was replaced by the corresponding BamHI/NdeI fragment of pTR27 (cf. Example 1). The resulting construct is called plS25. The DNA sequence analysis confirmed the correct insertion of the $His_6$ peptide between the amino acids $Thr_{35}$ and $Arg_{36}$.

The inducible overexpression of the pilC2 gene with the non-phase-variable nucleotide sequence and $His_6$ encoding nucleotide sequence was achieved by cloning the BamHI/HindIII fragment from the plS25 into the Hermes-8 vector (Kupsch et al., filed for publication) at first in E. coli K12 under the control of the Ptrc promoter (plS26, cf. FIG. 1), thus achieving the isopropyl-β-D-thiogalactoside (IPTG) inducible expression of the recombinant pilC2 genes under the control of the $P_{trc}$ promoters. By transformation of N. gonorrhoeae N219 and allelic exchange the shuttle box of plS26 containing the recombinant pilC2 gene was inserted into the conjugative plasmid ptetM25.2. This way the recombinant gene could be conjugatively transferred in the pilin-free N. gonorrhoeae strain N174, which, due to the deletion of the pilE gene coding for pilin, cannot be transformed. The resulting N. gonorrhoeae strain ISN19 synthesized after induction with IPTG pilin-free PilC2 protein in large amounts.

EXAMPLE 3

Isolation of Pilin-free, Biologically Active PilC Protein

For the recovery of the biologically active PilC protein of this invention the strain ISN19 was spread on 30 small GC-agar plates (9 cm in diameter) that contained an additional 5 µg/ml tetracycline and 100 µM IPTG and incubated for 20 hrs. at 37° C., 5% $CO_2$. The GC-agar plates contained the substances necessary for the growth of N. gonorrhoeae, particularly 36 g GC-Agar-Base (Becton, Dickinson & Company) which was autoclaved in 1 l water and to which 10 ml sterile-filtered vitamin mix were added. The vitamin mix particularly contained 0.01 g vitamin B12, 1 g adenine, 0.03 g guanine, 10 g glutamine, 0.1 g cocarboxylase, 0.03 g thiamine, 25.9 g L-cysteine, 1.1 g L-cystine, 150 mg arginine, 0.5 g uracil, 0.02 g $Fe(NO_3)_3$, 0.25 diphosphopyridin nucleotide, 0.013 g p-amino benzoic acid and 100 g dextrose dissolved in 1 l water. The bacteria were resuspended in 30 ml 50 mM TRIS.Cl, 0.15 M NaCl, pH 8.0 using cotton swabs and centrifuged for 15 minutes at 4,000 revolutions per minute (rpm) and 4° C. in a SS34 rotor (Sorval). The pellet was resuspended in 30 ml 50 mM TRIS.Cl, 0.15 M NaCl, pH 8.0, and the bacteria were broken up by addition of one spatula tip lysozyme and 5 mM ethylene diamine-tetraacidic acid-disodium salt-dihydrate (EDTA) by means of ultrasonic treatment. The lysed bacteria were pelleted for 20 minutes at 5,000 rpm and 4° C. in the SS34 rotor. The membranes were pelleted from the resulting supernatant for 60 minutes at 20,000 rpm and 4° C. in the SS34 rotor and then resuspended in 10 ml 50 mM TRIS.Cl, 0.15 M NaCl, 10% glycerin, 10 mM $MgCl_2$, pH 8.0 and 2% Triton X100. The suspension was incubated for 45 minutes at 37° C. and again centrifuged for 60 minutes at 20,000 rpm and 4° C. The membrane pellet, which consisted mainly of outer membrane, was washed once with 10 ml 50 mM TRIS.Cl, 0.15 M NaCl, pH 8.0 and again pelleted for 60 minutes at 20,000 rpm. Now the pellet was suspended in 10 ml 50 mM TRIS.Cl, 0.15 M NaCl, 10 mM $MgCl_2$, 10% glycerin, pH 8.0 and 2% LDAO (N,N-dimethyl dodecyl amine-N-oxide) and incubated for 60 minutes at 37° C. After centrifugation for 60 minutes at 20,000 rpm (4° C.) in the SS34 rotor the supernatant in which the biologically active PilC protein was dissolved and purified by means of nickel chelate affinity chromatography. For this purpose, a nickel-NTA (Ni-nitrilo triacidic acid)-agarose column containing 300 µl column volumes was prepared, washed with 5 volumes double-distilled water and 10 ml of the supernatant was applied with the extracted PilC protein. By washing the column with 300 µl 50 mM TRIS.Cl, 50 mM imidazole, 10% glycerin, pH 8.0 proteins unspecifically bound to the nickel-NTA-agarose column were removed. After washing the column with 5–10 volumes 20 mM $Na_xH_xPO_4$, 150 mM NaCl, pH 7.5 (PBS), the biologically active PilC protein was eluted using a citrate/phosphate buffer (10 mM citric acid, 1 M $Na_xH_xPO_4$, pH 3.5, 10% glycerin, 0.15 M NaCl). The eluate was immediately neutralized using a 1 M $Na_2HPO_4$ solution. The PilC protein of this invention contained in the eluate in pure form is shock frozen in liquid nitrogen and stored at −70° C.

EXAMPLE 4

Detection of a Receptor for PilC on Human Epithelial Cells

Pili-coupled fluorescent MX Covashere particles (FMP) were produced as follows: FMPs (Duke Scientific Corporation, Paolo Alto, Calif., U.S.A.) have a surface consisting of active groups that makes a direct, spontaneous coupling of proteins possible. In general, 100 µl of the FMPs having a diameter of 0.5 µm were mixed with approx. 2 µg purified pili (according to Jonsson et al., 1991) in 100 µl PBS and mixed on a rotation disk for 2 hrs. at room temperature. The pili-coated particles were pelleted and washed in 1 ml blocking buffer (20 mM TRIS.Cl with 2% fetuine, pH 7.5), to block the free coupling groups. The protein concentration in the supernatant after the first centrifugation was compared to the used amount of pili to determine the yield achieved by the coupling. More than 80% of the used pili were covalently bound to FMPs in this reaction. The particles were again pelleted and resuspended in 100 µl PBS. The FMPs were coated with purified pili of an adherent *Neisseria gonorrhoeae* wild-type strains (FMP-pilin/PilC), as well as coated with purified pili of a pilC1/2 deletion mutant (MS11-N474: Facius et al., filed for publication) (FMP-pilin) and with fetuine (FMP-fetuine; negative control). For the detection of PilC-protein specific receptors on human epithelial cells, the attachment of the pili-coated FMPs to epithelial cell lines was examined. These experiments were carried out analogously with gonococci to the standard infection protocol. Epithelial cells were cultivated in 24-well cell culture plates on sterile cover glasses in RPMI medium with 5% fetal bovine serum (FCS) at 37° C. and under 5% $CO_2$ fumigation. Preconfluent epithelial cell monolayers were washed with fresh medium before 10 µl of the pili-loaded FMP suspension per well were added. The adherence lasted for 1 hr., during which the cultures were incubated at 37° C. and 5% $CO_2$. Then free FMPs were removed by 5 times washing with PBS and immobilized using 2% paraformaldehyde in PBS for 30 minutes. The preparations could finally be observed under a Zeiss fluorescence microscope. The results of this test as shown in Table 1 show that in contrast to the wild-type pili, the PilC-free pili mediate no attachment to epithelial cells. The attachment of PilC-free pili to epithelial cells, however, may be complemented by adding the biologically active PilC2 protein of this invention. The addition of 2 µg biologically active PilC2 protein in 100 µl PBS to 100 µl of the already coated FMP pilin was followed by incubation for 2 hrs. at 20° C. under constant mixing. The particles were pelleted, washed in 1 ml PBS and resuspended in 100 µl PBS. The FMP pilin additionally coated with PilC protein are called FMP (pilin+PilC).

TABLE 1

| Attachment of fluorescent particles to human epithelial cells | |
|---|---|
| FMPs | FMPs per epithelial cell |
| FMP-Fetuine | 0.1–3 |
| FMP-Pilin/PilC | 150–400 |
| FMP-Pilin | 0.1–5 |
| FMP-(Pilin + PilC) | 100–300 |

Attachment of fluorescent particles (FMPS) to human epithelial cells. FMP fetuine, fetuine-coupled FMPs; FMP-pilin/PilC, FMPs coupled with purified pili of the *N. gonorrhoeae* strain N137; FMP pilin, FMPs coupled with purified pili of the *N. gonorrhoeae* strains N474; FMP (pilin+PilC), FMPs coupled with purified pili of the *N. gonorrhoeae* strain N474 that were additionally incubated with the PilC protein of this invention (Example 4). The results of the attachment are stated in the average amount of FMPs per epithelial cell.

EXAMPLE 5

Direct Detection of the Attachment of PilC to Receptors on Human Epithelial Cells For the detection of PilC-protein specific receptors on human epithelial cells, the attachment of the biologically active PilC protein of this invention to ME180 cells (human cervix carcinoma (ATCC HTB33)) was examined. The epithelial cells were cultivated at 37° C., 5% $CO_2$, in 4 Well Chamber Slides ™(Nunc) in RPMI medium using 5% fetal bovine serum (FCS). The addition of approx. 10 µg biologically active PilC protein at a maximal volume of 20 µl was followed by incubation for 30 minutes at 37° C. and 5% $CO_2$. Every well was washed three times with 1 ml PBS, then epithelial cells and bound PilC protein were immobilized for 30 minutes in 2% paraformaldehyde in PBS. To make bound PilC protein visible, immune fluorescence dyeing using specific anti serums against the biologically active PilC protein of this invention was carried out. These anti serums were obtained by means of immunization of Balb/c mice using the biologically active PilC protein of this invention. The fixated preparations were washed twice using 1 ml PBS and incubated with a dilution of 1:300 of the anti serums in PBS for 1 hr. The result was washed five times with PBS, 0.05% Tween20 in order to remove unspecifically bound antibodies (AK). To make the PilC AK complex visible, incubation was carried out for 60 minutes at 20° C. using a second AK directed against murine immuno globuline and marked with the fluorescent dye FITC, in a dilution of 1:2000 in PBS with 0.025% Tween20. Again, the resulting substance was thoroughly washed (5 times) with PBS, 0.05% Tween20, before the preparations were covered and analysed using a Zeiss fluorescence microscope. For negative control served (a) epithelial cells without PilC with second AK; (b) epithelial cells without PilC with first AK and second AK, and (c) epithelial cells with PilC and second AK. While the epithelial cells preincubated with the biologically active PilC protein of this invention were highly fluorescent after dyeing with specific PilC anti serums, they were only slightly fluorescent in all other monitoring experiments. For the purpose of further monitoring, the experiment was carried out with MDCK cells to which piliated Neisseria do not attach; correspondingly, no attachment of the PilC protein of this invention could be detected.

EXAMPLE 6
Competition of the Infection of Human Epithelial Cells with Neisseria Carrying out the in vitro infection and/or inhibition experiments takes place with preconfluent ME180-cells [human cervix carcinoma (ATCC HTB33)] that were cultivated on cover glasses in a 24 well cell culture plate. For the inhibition of the pilus-mediated adherence of *N. gonorrhoeae* and *N. meningitidis* the cells were incubated for 30 minutes at 37° C. and 5% $CO_2$ in 500 μl RPMI medium, 5% FCS by addition of 20 μg of the biologically active PilC protein. For infection the bacteria were incubated overnight at 37° C., 5% $CO_2$ on a GC plate and then resuspended in 1 ml RPMI Medium, 5% FCS using a cotton swab. The determination of the bacteria density is carried out using the spectro-photometer. The approximately $2 \times 10^5$ preconfluent epithelial cells were infected with $7 \times 10^7$ bacteria and incubated for 1 hr. at 37° C., 5% $CO_2$. Stopping the infection takes place by washing five times with preheated PBS followed by fixing the cells with 2% paraformaldehyde in PBS. The fixed cells were then dyed for at least 15 minutes at room temperature using crystal violet (0.07% w/v) and the adherent bacteria were determined per ME 180. As can be seen in Table 2, all tested piliated Neisseria strains adhered when the biologically active PilC2 protein was not present, whereas the non-piliated *N. gonorrhoeae* strain did not adhere. In the presence of the biologically active PilC2 protein the attachment of the tested piliated Neisseria strains was reduced to background level. Thus, the reduction of the attachment to epithelial cells takes place independent of the variant of the PilC protein naturally formed by the bacteria (PilC1 in TRN289, compared to PilC2 in TRN290, compared to an unknown PilC protein in *N. meningitidis* N530). This serves to (i) prove that the PilC protein is an important bacterial adhesin (i.e. it is essential for the occurrence of an infection), (ii) confirm the low variability of different PilC proteins regarding the recognition of cellular receptors and thus (iii) prove the suitability of the inhibitors of this invention for inhibiting the interaction between the PilC protein and its cellular receptors.

TABLE 2

Competition of the attachment of Neisseria to human epithelial cells

| Neisseria strains | Neisseria per epithelial cell Pretreatment of the epithelial cells | |
|---|---|---|
| | without PilC | 20 μg/ml PilC |
| N137 | 165 | — |
| N174 | — | — |
| TRN289 (pilE$_{N137}$; PilC1) | 140 | — |
| TRN290 (pilE$_{N137}$; PilC2) | 155 | — |
| N530 | 103 | — |

Competition of the attachment of pathogenic Neisseria to human epithelial cells. N137, piliated *N. gonorrhoeae* MS11 strain; N174, non-piliated strain derived from *N. gonorrhoeae* MS11 in which the pilE gene is deleted; TRN289, piliated *N. gonorrhoeae* MS11 strain that forms exclusively PilC1; TRN290, piliated *N. gonorrhoeae* MS11 strain that forms exclusively PilC2, and N530, *N. meningitidis* strain that forms an unknown PilC protein. The pretreatment of the epithelial cells with 20 μg/ml PilC2 protein of this invention is described in Example 6. The results of the competition experiment are stated in the average number of adherent bacteria per epithelial cell.

EXAMPLE 7
Identification of Other PilC-protein Encoding DNA Sequences

For the determination of the DNA sequence of the pilC2 genes, the BamHI/EcoRI fragment of the pTR27 was cloned into the bluescript SK vector (pTR34). With the exonuclease III suitable, overlapping deletion clones of pTR34 were produced and sequenced. The comparison of the DNA sequences coding for the PilC1 (A. Jonsson, Umea University, New Series No. 322, Department of Microbiology; ISSN 0346-6612) and those coding for the PilC2 protein (FIG. 4) using the computer program PCGENE/ ALGIN showed 84% identity. The regions of identical sequences distribute island-like over both genes with a clear concentration at the 3' terminal. With the aim to identify more sequences coding for PilC proteins, oligo nucleotide probes for the sequences identical between PilC1 and PilC2 were constructed. In the construct of the oligo nucleotide probes, particular care was taken to take turns in deriving the oligo nucleotides from the DNA (+) and (−) strands in order to be able to amplify corresponding fragments by means of PCR when necessary. This way, the entire DNA sequence of the pilC1 and pilC2 genes was divided up into overlapping fragments of approx. 400–500 bp. Besides, to every (+) strand oligo nucleotide the "M13mp" primer hybridization sequence was added at the 5' terminal, to every (−) strand oligo nucleotide the "M13mp reverse" primer (Vieira and Messing, Gene 19, 259–268, 1982) hybridization sequence was added at the 5' terminal to be able to directly identify the DNA sequence of the PCR fragment.

A selection of oligo nucleotide probes was marked with Biotin according to the regulations of the DIG oligo nucleotides tailing kit (Boehringer Mannheim) and used for hybridization against chromosomal DNA of *N. gonorrhoeae* digested with ClaI and PvuII. Southern Blot using the above-mentioned oligo nucleotide probes (Table 3) unambiguously indicated the existence of more pilC genes (besides pilC1 and pilC2) in the *N. gonorrhoeae* strain MS11 and in the *N. meningitidis* strain A1493. Furthermore, genes for PilC-analogous proteins were detected in a *Pseudomonas aeruginosa* strain using these probes. The such identified genes can now be cloned, characterized and further processed using standard techniques. This experiment proved that the described method is suitable for the identification of previously unknown genes for PilC and/or PilC analogous proteins.

TABLE 3

Oligo nucleotide probes for the identification of further PilC-protein encoding nucleotide sequences (SEQ. ID. NOS: 13–32)

| Oligo nucleotide | 5'Position pilC1/pilC2 | Sequence | +/-DNA strand |
|---|---|---|---|
| TR47 | 117/117 | TATTATCATGAACGAGCG | + |
| TR48 | 392/413 | CGGGTGGTACGAATCCAA | - |
| TR49 | 322/343 | AAGGTTTCCGGTTTTGATG | + |
| TR50 | 692/713 | ACGATGGTTTGATTATTA | - |
| TR51 | 590/611 | GCGTATCTTTCAATTTGG | + |
| TR52 | 1033/1060 | ACCACAGCGCGGGGCGGTCAG | - |
| TR53 | 935/965 | AGTCAAAGCAGGCCGCTG | + |
| TR54 | 1411/1423 | CCGTCCAAGGCAGCAGCAC | - |
| TR55 | 1327/1339 | AAAAACGACACTTTCGGC | + |
| TR56 | 1757/1799 | TCCACGCCGTAGCGGTCG | - |
| TR57 | 1630/1672 | AATCTGAAGCTCAGCTAC | + |
| TR58 | 2015/2072 | AGGAAGGCGGCGTATTTG | - |
| TR59 | 1957/2016 | TACACCGTCGGTACGCCGC | + |
| TR60 | 2329/2386 | CTGCCAGTCGGGAAACGGC | - |
| TR61 | 2253/2311 | TAGTAAATGGTCTGCAAAG | + |
| TR62 | 2611/2674 | TACGCAATACCACGGTCG | - |

TABLE 3-continued

Oligo nucleotide probes for the identification of further PilC-protein encoding nucleotide sequences (SEQ. ID. NOS: 13–32)

| Oligo nucleotide | 5'Position pilC1/pilC2 | Sequence | +/-DNA strand |
|---|---|---|---|
| TR63 | 2563/2626 | TTGAGGGAAGGAGAACGCG | + |
| TR64 | 2878/2941 | CCAG(G/A)TAACGCACATTAACC | - |
| TR65 | 2823/2886 | AACCGTCTGCCCGAACGG | + |
| TR66 | | TTCGGACGGCATTTGCGG | - |

Examples of oligo nucleotide probes for the identification of further PilC-protein encoding nucleotide sequences. Examples TR47–TR65 were taken from the sequence comparison of the *N. gonorrhoeae* genes pilC1 and pilC2 in FIG. 4A. TR66 corresponds to a sequence region downstream of the coding region of the pilC gene. The position numbers refer to the pilC1 and/or pilC2 genes in FIG. 4A.

What is claimed is:

1. An isolated DNA molecule comprising
   i) a first DNA fragment that is a heteropolymeric nucleotide sequence that encodes a homopolymeric amino acid sequence or that encodes a signal peptide and lacks a homopolymeric nucleotide sequence; and
   ii) a second DNA fragment that is a nucleotide sequence that encodes a mature PilC protein having at least one biological activity selected from the group consisting of supporting assembly of a type 4 pilus, mediating attachment of type 4 pili to a cellular receptor for type 4 pili and being immunogenic for induction of antibodies that block the attachment of type 4 pili to a cellular receptor for type 4 pili;
   wherein said first DNA fragment is operatively-linked to the 5' end of said second DNA fragment to prevent phase variation in the expression by a host cell of the protein encoded by said second DNA fragment.

2. The isolated DNA molecule of claim 1 wherein said first DNA fragment is a heteropolymeric nucleotide sequence that encodes a homopolymeric amino acid sequence.

3. The isolated DNA molecule of claim 2, wherein said homopolymeric amino acid sequence is poly-glycine.

4. The isolated DNA molecule of claim 2, wherein said homopolymeric amino acid sequence is 3 to 5 amino acids long.

5. The isolated DNA molecule of claim 1, wherein said second DNA fragment further comprises a nucleotide sequence that encodes a (histidine)$_6$ sequence.

6. The isolated DNA molecule of claim 2, wherein said second DNA fragment further comprises a nucleotide sequence that encodes a (histidine)$_6$ sequence.

7. The isolated DNA molecule of claim 5, wherein said nucleotide sequence encoding a (histidine)$_6$ sequence is attached at the 5'- or at the 3'-end of the nucleotide sequence encoding the mature PilC protein.

8. The isolated DNA molecule of claim 1, wherein said second DNA fragment comprises a nucleotide sequence selected from the group consisting of SEQ. ID. NOS. 1 to 32.

9. The isolated DNA molecule of claim 8, wherein said second DNA fragment comprises a nucleotide sequence selected from the group consisting of SEQ. ID. NOS. 1 to 3.

10. The isolated DNA molecule of claim 1, wherein said second DNA fragment comprises a nucleotide sequence that is obtained by amplifying a template DNA using a pair of primers, one member of said pair being selected from the group consisting of SEQ. ID. NO. 13, SEQ. ID. NO. 15, SEQ. ID. NO. 17, SEQ. ID. NO. 19, SEQ. ID. NO. 21, SEQ. ID. NO. 23, SEQ. ID. NO. 25, SEQ. ID. NO. 27, SEQ. ID. NO. 29 and SEQ. ID. NO. 31;

and the second member of said pair being selected from the group consisting of SEQ. ID. NO. 14, SEQ. ID. NO. 16, SEQ. ID. NO. 18, SEQ. ID. NO. 20, SEQ. ID. NO. 22, SEQ. ID. NO. 24, SEQ. ID. NO. 26, SEQ. ID. NO. 28, SEQ. ID. NO. 30 and SEQ. ID. NO. 32.

11. The isolated DNA molecule of claim 2, wherein said second DNA fragment comprises a nucleotide sequence that is obtained by amplifying a template DNA using a pair of primers, one member of said pair being selected from the group consisting of SEQ. ID. NO. 13, SEQ. ID. NO. 15, SEQ. ID. NO. 17, SEQ. ID. NO. 19, SEQ. ID. NO. 21, SEQ. ID. NO. 23, SEQ. ID. NO. 25, SEQ. ID. NO. 27, SEQ. ID. NO. 29 and SEQ. ID. NO. 31;

and the second member of said pair being selected from the group consisting of SEQ. ID. NO. 14, SEQ. ID. NO. 16, SEQ. ID. NO. 18, SEQ. ID. NO. 20, SEQ. ID. NO. 22, SEQ. ID. NO. 24, SEQ. ID. NO. 26, SEQ. ID. NO. 28, SEQ. ID. NO. 30 and SEQ. ID. NO. 32.

12. The isolated DNA molecule of claim 11, wherein said second DNA fragment further comprises a nucleotide sequence that encodes a (histidine)$_6$ sequence.

13. The isolated DNA molecule of claim 12, wherein said nucleotide sequence encoding a (histidine)$_6$ sequence is attached at the 5'- or at the 3'-end of the nucleotide sequence encoding the mature PilC protein.

14. The isolated DNA of claim 11, wherein said template DNA is obtained from a bacterium of the genus Neisseria.

15. A recombinant vector comprising the isolated DNA molecule of claim 1.

16. A recombinant vector comprising the isolated DNA molecule of claim 5.

17. A recombinant vector comprising the isolated DNA molecule of claim 11.

18. A recombinant vector comprising the isolated DNA molecule of claim 12.

19. The recombinant vector of claim 15, which further comprises a promoter that is functional in a Neisseria host cell that is operatively linked to said isolated DNA molecule so that said PilC protein is expressed by said host cell.

20. The recombinant vector of claim 16, which further comprises a promoter that is functional in a Neisseria host cell that is operatively linked to said isolated DNA molecule so that said PilC protein is expressed by said host cell.

21. The recombinant vector of claim 17, which further comprises a promoter that is functional in a Neisseria host cell that is operatively linked to said isolated DNA molecule so that said PilC protein is expressed by said host cell.

22. The recombinant vector of claim 18, which further comprises a promoter that is functional in a Neisseria host cell that is operatively linked to said isolated DNA molecule so that said PilC protein is expressed by said host cell.

23. A host cell transformed with the recombinant vector of claim 15.

24. A host cell transformed with the recombinant vector of claim 16.

25. A host cell transformed with the recombinant vector of claim 17.

26. A host cell transformed with the recombinant vector of claim 18.

27. A host cell transformed with the recombinant vector of claim 19.

28. A host cell transformed with the recombinant vector of claim 20.

29. A host cell transformed with the recombinant vector of claim 21.

30. A host cell transformed with the recombinant vector of claim 22.

31. A method for producing a PilC protein comprising culturing the host cell of claim 16 under conditions suitable for expression of said PilC protein and isolating the PilC so produced from the culture.

32. A method for producing a PilC protein comprising culturing the host cell of claim 18 under conditions suitable for expression of said PilC protein and isolating the PilC so produced from the culture.

* * * * *

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
        (A) LENGTH: 3270 base pairs
        (B) TYPE: nucleic acid
        (C) STRANDEDNESS: Not Relevant
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Neisseria gonorrheae (ix) FEATURE:
        (A) NAME/KEY: -
        (B) LOCATION: 1..3270
        (D) OTHER INFORMATION: /note= "PilC2"

(xi) SEQUENCE DESCRIPTION: SEQ ID NO:1:

```
GATCCTGCCG CCCCGAAGGG CGGGGGGTTT GACCGAAAAG GAAATACGAT GAATAAAACT      60

TTAAAAAGGC GGGTTTTCCG CCATACCGCG CTTTATGCCG CCATCTTGAT GTTTTCCCAT     120

ACCGGCGGGG GGGGGGGGGC GCAGGCGCAA ACCCGTAAAT ACGCTATTAT CATGAACGAG     180

CGAAAGCAGC CCGAGGTAAA GTGGGAGGGT CAATATAGTC AATCAACATT AAAGGACAAA     240

GGCAGGGAGC GGACATTTAG CCATACGAGC CAGAGAAACT GGAACGGCCA ACAAAACAAT     300

TTTATCTCAT TCAACAATAG CGATGAGCTT GTTTCCCGAC AAAGCGGTAC TGCCGTTTTT     360
```

```
GGCACAGCCA CCTACCTGCC GCCCTACGGC AAGGTTTCCG GTTTTGATGC CGACGGGCTG    420

AAAAAGCGCG GCAATGCCGT GAATTGGATT CGTACCACCC GGCCCGGGCT GGCAGGCTAC    480

ATCTACACCG GCGTCATATG CAGAGACACA GGGCAATGCC CCGAACTTGT CTATGAGACC    540

AAATTTTCCT TCGACGGCAT CGATTTGGCA AAAGGGGGAA ACCGAAAGCT GGATAGGCAC    600

CCGGACCCAA GCCGCGAAAA TTTGCCCATT TACAAATTGA AGGATCATCC ATGGTTGGGC    660

GTATCTTTCA ATTTGGCGG CGAGGGTACC GCCAAAGATG GCAGATCATC CAGCAGATGG    720

ATATCTTCTT TTAGTGAAGA CAATAATAAT CAAACCATCG TCTTTACGAC ACGAGGCCAC    780

CCTATTTCCC TTGGCGACTG GCAGCGCGAA AGTACCGCCA TGGCCTATTA TCTGGACGCC    840

AAACTGCACC TGCTGGATAA AACACAGATT GAAAATATCG CGCCAGGCAA ACAGTGAAT    900

TTGGGCATCT TGAGACCGCG CGTCGAGGCA AGGTAAGGC GGAAGTGGGA TCTGCTAAAT    960

TTTTGGGCTA AGTGGGACAT TAAAGATACC GGGCAGATTC CGGTCAAGCT CGGCCTGCCG   1020

GAAGTCAAAG CAGGCCGCTG CATCAACAAA CCGAACCCCA ATCCCAAATC AGCCCTTTCG   1080

CCGGCACTGA CCGCCCCCGC GCTGTGGTTC GGCCCTGTGC AAAATGGCAA GGTGCAGATG   1140

TATTCCGCTT CGGTTTCCAC CTACCCCGGC AGCTCGAGCA GCCGCATCTT CCTCCAAGAG   1200

CTGAAAACTA AAACCGACCC CGCCCGGCCC GGCCGGCATT CCCTCGCCGC TTTGAATGCG   1260

CAGGATATCA AATCCCGCGA GCCGAATTTC AACTCAAGGC AGACCGTCAT CCGATTGCCG   1320

GGCGGCGTGT ACCAGATCGC CCCGGGCAAT AGCGGCCGGG TCGCGGGTTT TAATGGCAAT   1380

GACGGCAAAA ACGACACTTT CGGCATCTAC AAGGACAGGC TCGTCACACC TGAGGTCGGC   1440

GAGTGGAGCG AAGTGCTGCT GCCTTGGACG GCCCGGTATT ACGGTAATGA CGATATATTT   1500

AAAACATTCA ACCAACCAAA CAGCAAAACA CAAAACGGCA AAAACAATA CAGCCAAAAA   1560

TACCGCATCC GCACAAAAGA AAATGACAAT GACAAACCCC GCGATTTGGG CGACATCGTC   1620

AACAGCCCGA TTGTCGCGGT CGGCGGGTAT CTGGCAACTT CTGCCAACGA CGGGATGGTG   1680

CATATCTTCA AAAAACCGG CACGGATGAA CGCAGCTACA ATCTGAAGCT CAGCTACATC   1740

CCCGGTACGA TGGAGCGTAA GGATATTGAA GGCAATGACT CCGACCTCGC CAAAGAGCTG   1800

CGCACCTTTG CCGAAAAAGG CTATGTGGGC GACCGCTACG GCGTGGACGG CGGCTTTGTC   1860

TTGCGCCGCA TTACAGATGA CCAAGACAAG CAAAAACATT TCTTTATGTT TGGTGCGATG   1920

GGCCTGGGCG GCAGAGGCGC GTATGCCTTG GATTTAAGCA AAATCGACAG CAGCAACCTG   1980

ACCGGCGTTT CCATGTTTGA TGTCCAAAAC GACAAAAATA ACAATAACAA TAAGAATGAC   2040

AATAATCGCG TGAAATTAGG CTACACCGTC GGTACGCCGC AAATCGGCAA ACCCAAAAC   2100

GGCAAATACG CCGCCTTCCT CGCTTCCGGT TATGCGGCTA AAAATATTGG CAGCGGCGAT   2160

AATACAACCG CGCTGTATGT GTATGATTTG GAAAACACCA GTGGTAGTCT GATTAAAAAA   2220

ATCGAAGCAC CCGGCGGCAA AGGCGGGCTT TCGTCCCCCA CGCTGGTGGA TAAAGATTTG   2280

GACGGCACGG TCGATATCGC CTATGCCGGC GACCGGGGCG GCAATATGTA CCGCTTTGAT   2340

TTGAGCAATT CCGATTCTAG TAAATGGTCT GCAAGGTTA TTTTCGAAGG CGACAAGCCG   2400

ATTACCTCCG CGCCCGCCGT TTCCCGACTG GCAGACAAAC GCGTGGTTAT CTTCGGCACG   2460

GGCAGCGATT TGAGTGAACA GGATGTACTG GATACGGACA AACAATATAT TTACGGTATC   2520

TTTGACGACG ATAAGTCGAC GGTTAATGTA AAGGTAACAA ACGGCACGGG AGGCGGGCTG   2580

CTCGAGCAAG TGCTTAAAGA GGAAAGTAAA ACCTTATTCC TGAGCAATAA TAAGGCATCC   2640

GGCGGATCGG CCGATAAAGG GTGGGTAGTG AAATTGAGGG AAGGAGAACG CGTTACCGTC   2700
```

-continued

```
AAACCGACCG TGGTATTGCG TACCGCCTTT GTCACCATCC GCAAATATAC GGATACGGAC    2760

AAATGTGGCG CGCAAACCGC CATTTTGGGC ATCAATACCG CCGACGGCGG CGCATTGACT    2820

CCGAGAAGCG CGCGCCCGAT TGTGCCGGAT CACAATTCGG TTGCGCAATA TTCCGGCCAT    2880

CAGAAAATGA ACGGCAAGTC CATCCCCATA GGCTGCATGT GGAAAAACAG CAAAACCGTC    2940

TGCCCGAACG GATATGTTTA CGACAAACCG GTTAATGTGC GTTACCTGGA CGAAAAGAAA    3000

ACAGACGATT TCCCCGTCAC GGCAGACGGT GATGCAGGCG GCAGCGGAAC ATTCAAAGAG    3060

GGTAAAAAAC CCGCCCGCAA TAACCGGTGC TTCTCCGGAA AAGGTGTGCG CACCCTGCTG    3120

ATGAACGATT TGGACAGCTT GGATATTACC GGCCCGATGT GCGGTATCAA ACGCTTAAGC    3180

TGGCGCGAAG TCTTCTTCTG ACCCGCCTGC GCGGCCGGTT TTTCCGCAAA TCCCGTCCGA    3240

AAGGTCTTCG GACGGCATTT TTTTGCGTTT                                    3270
```

(2) INFORMATION FOR SEQ ID NO:2:

(i) SEQUENCE CHARACTERISTICS:
        (A) LENGTH: 3114 base pairs
        (B) TYPE: nucleic acid
        (C) STRANDEDNESS: Not Relevant
        (D) TOPOLOGY: Not Relevant (ii) MOLECULE TYPE: DNA (genomic)

(iii) HYPOTHETICAL: NO (vi) ORIGINAL SOURCE:
        (A) ORGANISM: Neisseria meningitidis (ix) FEATURE:
        (A) NAME/KEY: -
        (B) LOCATION: 1..3114
        (D) OTHER INFORMATION: /note= "PilC A1493"

(xi) SEQUENCE DESCRIPTION: SEQ ID NO:2:

```
ATGAATAAAA CTTTAAAAAG GCAGGTTTTC CGCCATACCG CGCTTTATGC CGCCATCTTG      60

ATGTTTTCCC ATACCGGCGG GGGGGGGCG ATGGCGCAAA CCCATAAATA CGCTATTATC     120

ATGAACGAGC GAAACCAGCT CGAGGTAAAG GGGAATGGGC AATATTCAAC AATAAAGGAC     180

AAAGACAGGG AACGCAAATT TATCTATAAT AAAGACAGAG GGGGTGGAGG CTCTGTCTTT     240

TTCGACAATA CCGATACCCT TGTTTCCCAA CAAAGAGGTA CTGCCGTTTT TGGCACAGCC     300

ACCTACCTGC CGCCCTACGG CAAGGTTTCC GGTTTTGATG CCGACGGGCT GCAAAAGCGC     360

AACAATGCCG TCGATTGGAT TCATACCACC CAGGCCGGGC TGGCAGGCTA CGCCTACACC     420

GACGTCATAT GCAGAAGCAA CCAATGCCCC CAACTTGTCT ATGAGACCAA ATTTTCCTTC     480

GACGGCATCG GTTTGGCAAA AAATGCGGGC AGCCTGGATA GGCACCCGGA CCCAAGCCGC     540

GAAAATTCGC CCATTTACAA ATTGAAAGAT CATCCATGGT TGGGCGTATC TTTCAATTTG     600

GGCAGCGAGA ATACCGTCAA AGATGGCAAA TCATTCAACA AATTGATATC TTCTTTTAGT     660

GAAGGCAATA ATAATCAAAC CATCGTCTCT ACGACACGAG GCCACTCTAT TTCCCTTAGC     720

GACTGGAAGC GCGAACATAC CGCCATGGCC TATTATCTGA ACGCCAAACT GCACCTGCTG     780

GACAAAAAAG GGATTGAAGA TATCGCCCAA GGCAAAACAG TGGATTTGGG CACCTTGAGA     840

CCGCGCGTCG AGGCAACGGT AAGGCGGGG GAGCTGCTAA ATTTTTGGGC TACGTGGAAG     900

ATTGAAGATA AAGGGAACAT TACAGTCCGC CTCGGCCTGC CGGAAGTCAA AGCAGGCCGC     960

TGCGTCAACA AAGCGAACCC CAATCCCAAC GCCAAAGCCC CCTCCCCCGC ACTGACCGCC    1020

CCCGCGCTGT GGTTCGGACC TGTGAAAGAT GGTAAGGCGG AGATGTATTC CGCTTCGGTT    1080
```

-continued

```
TCTACCTACC CCGACAGTTC GAGCAGCCGC ATCTACCTTC AAAATCTGAA AAGAAAAACC    1140

GACCCCGGCA AACCCGGCCG CCATTCCCTC GAAACCTTGA CTGAGAATGA TATTAAAAGT    1200

CGAGAGCCGA ATTTCACAGG GCGGCAAACC ATCATCCGAT TGAATGGCGG CGTACGTGAG    1260

ATCAAACTGG ATAGAAACAA TACTGAGGTC GTCAATTTTA ATGGAAATGA CGGCAACAAC    1320

GACACTTTCG GCATTGTTAA GGACTTGGGC GTCGAACCTG ATACCAGCGA GTGGAAAAAA    1380

GTATTGCTGC CTTGGACGGT TCGGGGTTTT GCTGATGACA ATAAATTTAA AGCATTCAAC    1440

AAAGAAGAAA ACAACGACAA CAAGCCAAAA TACAGCCAAA AATACCGCAG CCGCGACAAC    1500

AACAAGGGCG AACGCAATTT GGGCGACATC GTCAACAGCC CCATCGTGGC GGTCGGCGAG    1560

TATTTGGCTA CTTCCGCCAA CGACGGGATG GTGCATATCT TCAAACAAAG CGGCGGGGAC    1620

AAGCGCAGCT ACAATCTGAA GCTCAGCTAC ATCCCTGGAA CGATGCCGCG CAAGGATATT    1680

CAAAACACCG AATCCACCCT TGCCAAAGAC GTGCGCACCT TTGCCGAAAA AGGCTATGTG    1740

GGCGACCGCT ACGGCGTGGA CGGCGGCTTT GTCTTGCGCA AAGTTGATAA CTTAAACGGG    1800

CAAAACCGCG TGTTTATGTT CGGCGCGATG GGCTTTGGCG GCAGAGGCGC GTATGCCTTG    1860

GATTTGACCA AAGCCGACGG CAGTGACCCG ACCGCCGTTT CCCTGTTTGA TGTAAAAGAT    1920

AACGGCAATA ATGGCAATAA TCGCGTGGAA TTAGGCTACA CCGTCGGCAC GCCGCAAATC    1980

GGCAAAACCC ACGACGGCAA ATACGCCGCC TTCCTCGCCT CCGGTTATGC GACTAAAGAA    2040

ATTATTACCA GCGGCGACAA TAAAACCGCG CTGTATGTGT ATGATTTGGA AGGAAACGGT    2100

ACGAATAATC TGATTAAAAA AATCGAAGTA CCCGGCGGCA AGGGCGGGCT TTCGTCCCCC    2160

ACGCTGGTGG ATAAAGATTT GGACGGCACG GTCGATATCG CCTATGCCGG CGATCGCGGC    2220

GGGAATATGT ACCGCTTTGA TTTGAGCAGT CAAGATCCTC AACAATGGTC TGTACGCACT    2280

ATTTTTGAAG GCACAAAACC GATTACTTCC GCGCCCGCTA TTTCCCAACT GAAAGACAAA    2340

CGCGTGGTCA TCTTCGGCAC GGGCAGCGAT TTGAGTGAAG AGGATGTGGA CAATATGGAA    2400

GAACAATATA TTTACGGTAT CTTCGACGAC GATACGGCGA CGACGGGTAC TGTAAACTTC    2460

AGCGATTCGG GAGGCGGGCT GCTTGAGCAA GTGCTTCGTA GGGATAACGA CAATAAAACC    2520

TTATTCCTGA CCGATTACAA GCGATCCGAC GGATCGGGCA ATAAGGGCTG GGTAGTGAAA    2580

TTGAAGGACG GACAGCGCGT TACCGTCAAA CCGACCGTGG TATTGCGTAC CGCCTTTGTA    2640

ACCATCCATA AATATACGGG TACGGACAAA TGCGGCGCGG AAACCGCCAT TTTGGGCATC    2700

AATACCGCCG ACGGCGGCAA GCTGACCAAG AAAAGCGCGC GCCCGATTGT GCCGGAAGCC    2760

AATACGGCTG TCGCGCAATA TTCCGGCCAT AAGAAAGGCA CCAACGGCAA ATCCATCCCT    2820

ATAGGTTGTA TGCAAAAAAG CAATGAAATC GTCTGCCCGA ACGGATATGT TTACGACAAA    2880

CCGGTTAATG TGCGTTATCT GGATGAAAAG AAAACAGACG GATTTTCAAC AACGGCAGAC    2940

GGCGATGCGG GCGGCAGCGG TATAGACCCC GCCGGCAAGC GTTCCGGCAA AAACAACCGC    3000

TGCTTCTCCC AAAAAGGGGT GCGCACCCTG CTGATGAACG ATTTGGACAG CTTGGACATT    3060

ACCGGCCCGA CGTGCGGTAT GAAACGAATC AGCTGGCGTG AAGTCTTCTA CTGA         3114
```

(2) INFORMATION FOR SEQ ID NO:3:

(i) SEQUENCE CHARACTERISTICS:
        (A) LENGTH: 3567 base pairs
        (B) TYPE: nucleic acid
        (C) STRANDEDNESS: Not Relevant
        (D) TOPOLOGY: Not Relevant (ii) MOLECULE TYPE: DNA (genomic)

(iii) HYPOTHETICAL: NO (vi) ORIGINAL SOURCE:
    (A) ORGANISM: Neisseria gonorrheae (ix) FEATURE:
    (A) NAME/KEY: -
    (B) LOCATION: 1..3567
    (D) OTHER INFORMATION: /note= "PilC1 gene"

(xi) SEQUENCE DESCRIPTION: SEQ ID NO:3:

```
GATCCGCCCG GTGCTTGGGC GCCTTAGGGA ACCGTTCCCT TTGAGCCGGG GCGGGGCAAC    60

GCCGTACCGG TTTTTGTTAA TCCGCTATAA AAGGCGGGCT ATAGGGTAGG CTTCATCCTG   120

CCAATCTCAC TGAATCCGTC AATTTCCGCA ATTCAATTAA ATACCGTCAA ACCGATGCCG   180

TCATTCCGCG CAGGCGGGAA TCCGGACCGG TCGGGCATCT GCGGCGGTTT GCTAAAAAAC   240

GCTTTACCGT GATAAGTGCG CAAAGTTAAA ATGGGGAGGT AAGCTTTTCA ATCAGCAATC   300

CGGCGGGCGC GGAATCGGGC GGTTTACCGA ACCCCGGCGT TCGCGGCGCC CGTCCCGCGA   360

AGGCAAACTT AAGGAATAAA ATATGAATAA AACTTTGAAA CGGCAGGTTT TCCGCCATAC   420

CGCGCTTTAT GCCGCCATCT TGATGTTTTC CCATACCGGC GGGGGGGGGG GGCGATGGCG   480

CAAACCCATC AATACGCTAT TATCATGAAC GAGCGAAACC AGCCCGAGGT AAAGCAGAAT   540

GTGCCATCTT CAATAAAGGA CAAAGACAGG AGGCGCGAAT ATACTTATTA TACGCACAGA   600

ACAGGAGCAG GCTCTGTCTC ATTCAACAAT AACGATACCC TTGTTTCCCA ACAAAGCGGT   660

ACTGCCGTTT TTGGCACAGC CACCTACCTG CCGCCCTACG GCAAGGTTTC CGGTTTTGAT   720

GCCGTCGCTC TGAAAGAGCG CAACAATGCC GTTGATTGGA TTCGTACCAC CCGCATCGCG   780

CTGGCAGGCT ACTCCTACAT CGACGTCATA TGCAGAAGCT ACACAGGCTG TCCCAAACTT   840

GTCTATAAAA CCCGATTTAC CTTCGGTCAA CAAGGGTTGA AAAGAAAGGC AGGCAGCAAG   900

CTGGATATAT ACGAAGACAA AAGCCGCGAA AATTCGCCCA TTTACAAATT GTCGGATTAT   960

CCTTGGTTGG GCGTATCTTT CAATTTGGGC AGCGAGAATA CCGTCCAAAA TAGCAAATTA  1020

TTCAACAAAT TGATATCTTC TTTTAGAGAA GGCAATAATA ATCAAACCAT CGTCTCTACG  1080

ACAGAAGGCA ACCCTATTTC CCTTGGCGAC CGGCAGCGCG AACATACCGC CGTGGCCTAT  1140

TATCTGAACG CCAAACTGCA CCTGCTGGAC AAAAAAGGGA TTGAAGATAT CGCCCAAGGC  1200

AAAATAGTGG ATTTGGGTAT CTTGAAACCG CACGTCGAGA CGACAGGACG AAGCTTGCTA  1260

GATTTTTGGG CTAGGTGGGA CATTAAAGAT ACCGGGCAGA TTCCGGTCAA GCTCGGCCTG  1320

CCGCAAGTCA AGCAGGCCG CTGCACCAAC AAACCGAACC CCAATAATAA TACCAAAGCC  1380

CCTTCGCCGG CACTGACCGC CCCCGCGCTG TGGTTCGGAC CCGGGCAAGA TGGTAAGGCG  1440

GAGATGTATT CCGCTTCGGT TTCCACCTAC CCCGACAGTT CGAGCAGCCG CATCTTCCTC  1500

CAAGAGCTGA AAACTCAAAC CGAACCCGGC AAACCCGGCC GCTATTCCCT CAAATCTTTG  1560

AATGATGGTG AGATTAAAAG TCGACAGCCG AGTTTCAACG GCGGCAAAC AATCATCCGA  1620

TTGGATGACG GCGTACATTT GATCAAACTG AATGGAAGCA AGGATGAGGT CGCCGCTTTT  1680

GTCAATTTAA ATGGAAACAA CACCGGCAAA AACGACACTT TCGGCATTGT TAAGGAAGCG  1740

AACGTCAATC TTGACGCCGA CGAGTGGAAA AAAGTGCTGC TGCCTTGGAC GGTTCGGGGT  1800

CCCGATAATG ACAATAAATT TAAATCAATT AACCAAAAAC CAGAAAAATA CAGCCAAAGA  1860

TACCGCATCC GCGACAACAA CGGCAATCGC GATTTGGGCG ACATCGTCAA CAGCCCGATT  1920

GTCGCGGTCG GCGGGTATTT GGCAACCGCC GCGAACGACG GGATGGTGCA TATCTTCAAA  1980

AAAAACGGCG GCAGTGATGA ACGCAGCTAC AATCTGAAGC TCAGCTACAT CCCCGGCACG  2040
```

```
ATGCCGCGCA AGGATATTCA AAGCCAAGAA TCCACCCTTG CCAAAGAGCT GCGCGCCTTT      2100

GCCGAAAAAG GCTATGTGGG CGACCGCTAC GGCGTGGACG GCGGCTTTGT CTTGCGCCAA      2160

GTCGAACTGA GCGGGCAAAA ACACGTGTTT ATGTTCGGCG CGATGGGTTT TGGCGGCAGG      2220

GGCGCGTATG CCTTGGATTT AAGCAAAATC AACGGAAATT ATCCGGCCGC CGCCCCCCTG      2280

TTTGATGTCA AAGATGGCGA TAATAACGGC AAAAATCGCG TGAAAGTGGA ATTAGGCTAC      2340

ACCGTCGGTA CGCCGCAAAT CGGCAAAATC CGCAACGGCA AATACGCCGC CTTCCTCGCC      2400

TCCGGTTATG CGGCTAAAAA AATTGACGAC TCAACAAATA AAACCGCGCT GTATGTATAT      2460

GATTTGAAAG ACACCTTAGG TACGCCGATT GCAAAAATCG AAGTGAAGGA CGGCAAAGGC      2520

GGGCTTTCGT CCCCCACGCT GGTGGATAAA GATTTGGACG GCACGGTCGA TATCGCCTAT      2580

GCCGGCGACC GGGGCGGCAA TATGTACCGC TTTGATTTGA GCAATTCCGA TTCTAGTAAA      2640

TGGTCTGCAA AGGTTATTTT CGAAGGCGAC AAGCCGATTA CCTCCGCGCC CGCCGTTTCC      2700

CGACTGGCAG ACAAACGCGT CGTCATCTTC GGTACGGGCA GCGATTTGAC CGAAGATGAT      2760

GTACTGAATA CGGGCGAACA ATATATTTAC GGTATCTTTG ACGACGATAA GGGGACGGTT      2820

AAGGTAACGG TACAAAACGG CACGGCAGGC GGGCTGCTCG AGCAACACCT TACTCAGGAA      2880

AATAAAACAT TATTCCTGAA CAAGAGATCC GACGGTTCGG GCAGCAAGGG CTGGGCGGTG      2940

AAATTGAGGG AAGGAGAACG CGTTACCGTC AAACCGACCG TGGTATTGCG TACCGCCTTC      3000

GTAACCATCC GCAAATATAA CGACGGCGGC TGCGGCGCGG AAACCGCCAT TTTGGGCATC      3060

AATACCGCCG ACGGCGGCGC ATTGACTCCG AGAAGCGCGC GCCCGATTGT GCCGGATCAC      3120

AATTCGGTTG CGCAATATTC CGGCCATAAG ACAACCTCCA AAGGCAAATC CATCCCTATA      3180

GGTTGTATGG ACAAAGACGG TAAAACCGTC TGCCCGAACG GATATGTTTA CGACAAGCCG      3240

GTTAATGTGC GTTATCTGGA TGAAACGGAA ACAGACGGAT TTTCAACGAC GGCGGACGGC      3300

GATGCGGGCG GCAGCGGTAT AGACCCCGCC GGCAGGCGTC CCGGCAAAAA CAACCGCTGC      3360

TTCTCCAAAA AAGGGGTGCG CACCCTGCTG ATGAACGATT TGGACAGCTT GGATATTACC      3420

GGCCCGATGT GCGGTATCAA ACGCTTAAGC TGGCGCGAAG TCTTCTTCTG ACCGGCCTGC      3480

GCGGCCGGTT TTTCCGCAAA TGCCGTCCGA AAGGCCTTCG GACGGCATTT TTTTGCGTTT      3540

TTCGGGAGGG GGGCGGCAAA TGAAACG                                          3567
```

(2) INFORMATION FOR SEQ ID NO:4:

(i) SEQUENCE CHARACTERISTICS:
        (A) LENGTH: 13 base pairs
        (B) TYPE: nucleic acid
        (C) STRANDEDNESS: Not Relevant
        (D) TOPOLOGY: Not Relevant (ii) MOLECULE TYPE: DNA (genomic)

(iii) HYPOTHETICAL: NO (ix) FEATURE:
        (A) NAME/KEY: misc_feature
        (B) LOCATION: 1..13
        (D) OTHER INFORMATION: /note= "example homopolymeric basis
            for "invariable heteropolymeric nucleotide sequence""

(xi) SEQUENCE DESCRIPTION: SEQ ID NO:4:

GGGGGGGGGG GGG                                                                  13

(2) INFORMATION FOR SEQ ID NO:5:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide probe CG31"

(iii) HYPOTHETICAL: NO (xi) SEQUENCE DESCRIPTION: SEQ ID NO:5:

CGATGGCGCA AACCCATCAA                                                  20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide probe CG32"

(xi) SEQUENCE DESCRIPTION: SEQ ID NO:6:

CGCAGGCGCA AACCCGTAAA                                                  20

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer TR12"

(xi) SEQUENCE DESCRIPTION: SEQ ID NO:7:

TTGGATCCGA CGTCCGAAAA GGAAATACGA TG                                    32

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer TR28"

(xi) SEQUENCE DESCRIPTION: SEQ ID NO:8:

GCTCCACCAC CTCCGCCGGT ATGGGAAAAC                                       30

(2) INFORMATION FOR SEQ ID NO:9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer TR27"

(xi) SEQUENCE DESCRIPTION: SEQ ID NO:9:

ACCGGCGGAG GTGGTGGAGC GCAGGCGCAA ACCCGT                                36
```

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer TR23"

(xi) SEQUENCE DESCRIPTION: SEQ ID NO:10:

```
TGTGTCTCTG CATATGACG                                             19
```

(2) INFORMATION FOR SEQ ID NO:11:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer TR71"

(xi) SEQUENCE DESCRIPTION: SEQ ID NO:11:

```
GTGATGATGG TGGTGATGGG TTTGCGCCTG CGCTCCA                         37
```

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer TR70"

(xi) SEQUENCE DESCRIPTION: SEQ ID NO:12:

```
CATCACCACC ATCATCACCG TAAATACGCT ATTATC                          36
```

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer TR47"

(xi) SEQUENCE DESCRIPTION: SEQ ID NO:13:

```
TATTATCATG AACGAGCG                                              18
```

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer TR48"

(xi) SEQUENCE DESCRIPTION: SEQ ID NO:14:

```
CGGGTGGTAC GAATCCAA                                              18
```

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer TR49"

(xi) SEQUENCE DESCRIPTION: SEQ ID NO:15:

AAGGTTTCCG GTTTTGATG                                      19

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer T50"

(xi) SEQUENCE DESCRIPTION: SEQ ID NO:16:

ACGATGGTTT GATTATTA                                       18

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer TR51"

(xi) SEQUENCE DESCRIPTION: SEQ ID NO:17:

GCGTATCTTT CAATTTGG                                       18

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer T52"

(xi) SEQUENCE DESCRIPTION: SEQ ID NO:18:

ACCACAGCGC GGGGGCGGTC AG                                22

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer T53"

(xi) SEQUENCE DESCRIPTION: SEQ ID NO:19:

AGTCAAAGCA GGCCGCTG                                                          18

(2) INFORMATION FOR SEQ ID NO:20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer T54"

(xi) SEQUENCE DESCRIPTION: SEQ ID NO:20:

CCGTCCAAGG CAGCAGCAC                                                         19

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer T55"

(xi) SEQUENCE DESCRIPTION: SEQ ID NO:21:

AAAAACGACA CTTTCGGC                                                          18

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer T56"

(xi) SEQUENCE DESCRIPTION: SEQ ID NO:22:

TCCACGCCGT AGCGGTCG                                                          18

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer T57"

(xi) SEQUENCE DESCRIPTION: SEQ ID NO:23:

AATCTGAAGC TCAGCTAC                                                          18

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer TR58"

(xi) SEQUENCE DESCRIPTION: SEQ ID NO:24:

```
AGGAAGGCGG CGTATTTG                                                  18

(2) INFORMATION FOR SEQ ID NO:25:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer T59"

(xi) SEQUENCE DESCRIPTION: SEQ ID NO:25:

TACACCGTCG GTACGCCGC                                                 19

(2) INFORMATION FOR SEQ ID NO:26:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer T60"

(xi) SEQUENCE DESCRIPTION: SEQ ID NO:26:

CTGCCAGTCG GGAAACGGC                                                 19

(2) INFORMATION FOR SEQ ID NO:27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer T61"

(xi) SEQUENCE DESCRIPTION: SEQ ID NO:27:

TAGTAAATGG TCTGCAAAG                                                 19

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer TR62"

(xi) SEQUENCE DESCRIPTION: SEQ ID NO:28:

TACGCAATAC CACGGTCG                                                  18

(2) INFORMATION FOR SEQ ID NO:29:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer TR63"
```

(xi) SEQUENCE DESCRIPTION: SEQ ID NO:29:

TTGAGGGAAG GAGAACGCG                                                  19

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer TR64"

(xi) SEQUENCE DESCRIPTION: SEQ ID NO:30:

CCAGRTAACG CACATTAACC                                                 20

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer TR65"

(xi) SEQUENCE DESCRIPTION: SEQ ID NO:31:

AACCGTCTGC CCGAACGG                                                   18

(2) INFORMATION FOR SEQ ID NO:32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer T66"

(xi) SEQUENCE DESCRIPTION: SEQ ID NO:32:

TTCGGACGGC ATTTGCGG                                                   18

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: Not Relevant
        (D) TOPOLOGY: linear (ii) MOLECULE TYPE: cDNA to mRNA (iii) HYPOTHETICAL: NO (iv) ANTI-SENSE: NO (ix) FEATURE:
        (A) NAME/KEY: CDS
        (B) LOCATION: 1..24

(xi) SEQUENCE DESCRIPTION: SEQ ID NO:33:

CAT ACC GGC GGG GGG GGG GGG GCG                                       24
His Thr Gly Gly Gly Gly Gly Ala
  1               5

(2) INFORMATION FOR SEQ ID NO:34:

(i) SEQUENCE CHARACTERISTICS:
         (A) LENGTH: 8 amino acids
         (B) TYPE: amino acid
         (D) TOPOLOGY: linear (ii) MOLECULE TYPE: protein (xi) SEQUENCE DESCRIPTION: SEQ ID NO:34:

His Thr Gly Gly Gly Gly Gly Ala
 1               5

(2) INFORMATION FOR SEQ ID NO:35:

(i) SEQUENCE CHARACTERISTICS:
         (A) LENGTH: 24 base pairs
         (B) TYPE: nucleic acid
         (C) STRANDEDNESS: Not Relevant
         (D) TOPOLOGY: linear (ii) MOLECULE TYPE: cDNA to mRNA (iii) HYPOTHETICAL: NO (ix) FEATURE:
         (A) NAME/KEY: CDS
         (B) LOCATION: 1..24

(xi) SEQUENCE DESCRIPTION: SEQ ID NO:35:

CAT ACC GGT GGA GGT GGT GGA GCG                                         24
His Thr Gly Gly Gly Gly Gly Ala
    10              15

(2) INFORMATION FOR SEQ ID NO:36:

(i) SEQUENCE CHARACTERISTICS:
         (A) LENGTH: 8 amino acids
         (B) TYPE: amino acid
         (D) TOPOLOGY: linear (ii) MOLECULE TYPE: protein (xi) SEQUENCE DESCRIPTION: SEQ ID NO:36:

His Thr Gly Gly Gly Gly Gly Ala
 1               5

(2) INFORMATION FOR SEQ ID NO:37:

(i) SEQUENCE CHARACTERISTICS:
         (A) LENGTH: 24 base pairs
         (B) TYPE: nucleic acid
         (C) STRANDEDNESS: Not Relevant
         (D) TOPOLOGY: linear (ii) MOLECULE TYPE: cDNA to mRNA (iii) HYPOTHETICAL: NO (ix) FEATURE:
         (A) NAME/KEY: CDS
         (B) LOCATION: 1..24

(xi) SEQUENCE DESCRIPTION: SEQ ID NO:37:

GCG CAG GCG CAA ACC CGT AAA TAC                                         24
Ala Gln Ala Gln Thr Arg Lys Tyr
    10              15

(2) INFORMATION FOR SEQ ID NO:38:

(i) SEQUENCE CHARACTERISTICS:
         (A) LENGTH: 8 amino acids

```
            (B) TYPE: amino acid
            (D) TOPOLOGY: linear (ii) MOLECULE TYPE: protein (xi) SEQUENCE DESCRIPTION: SEQ ID NO:38:

Ala Gln Ala Gln Thr Arg Lys Tyr
  1               5

(2) INFORMATION FOR SEQ ID NO:39:

(i) SEQUENCE CHARACTERISTICS:
            (A) LENGTH: 24 base pairs
            (B) TYPE: nucleic acid
            (C) STRANDEDNESS: Not Relevant
            (D) TOPOLOGY: linear (ii) MOLECULE TYPE: cDNA to mRNA (iii) HYPOTHETICAL: NO (ix) FEATURE:
            (A) NAME/KEY: CDS
            (B) LOCATION: 1..24

(xi) SEQUENCE DESCRIPTION: SEQ ID NO:39:

ACC CAT CAC CAC CAT CAT CAC CGT                                        24
Thr His His His His His His Arg
         10                  15

(2) INFORMATION FOR SEQ ID NO:40:

(i) SEQUENCE CHARACTERISTICS:
            (A) LENGTH: 8 amino acids
            (B) TYPE: amino acid
            (D) TOPOLOGY: linear (ii) MOLECULE TYPE: protein (xi) SEQUENCE DESCRIPTION: SEQ ID NO:40:

Thr His His His His His His Arg
  1               5
```